United States Patent
Lingren

[19]

[11] Patent Number: 6,018,905
[45] Date of Patent: Feb. 1, 2000

[54] KAIROMONE INSECT TRAP FOR CAPTURE OF CORN ROOTWORM

[75] Inventor: Bill W. Lingren, Carmel Valley, Calif.

[73] Assignee: Trece, Inc., Salinas, Calif.

[21] Appl. No.: 09/047,191

[22] Filed: Mar. 19, 1998

Related U.S. Application Data

[60] Provisional application No. 60/041,305, Mar. 19, 1997.

[51] Int. Cl.[7] .............................. A01M 1/20; A01M 5/00
[52] U.S. Cl. ................................ 43/107; 43/133
[58] Field of Search .............................. 43/107, 108, 121,
43/122, 117, 133; 119/428, 429, 433, 430,
431, 432, 434, 435; 47/83, 87

[56] References Cited

U.S. PATENT DOCUMENTS

| | | | |
|---|---|---|---|
| 1,185,345 | 5/1916 | Reiber | 119/430 |
| 1,312,573 | 8/1919 | Pichot | 43/122 |
| 1,634,763 | 7/1927 | Troski | 119/430 |
| 1,752,597 | 4/1930 | Jackson | 119/430 |
| 1,772,989 | 8/1930 | Emley | 43/122 |
| 1,916,878 | 7/1933 | Anklam | 119/430 |
| 2,715,295 | 8/1955 | Brown | 43/122 |
| 2,809,465 | 10/1957 | Guinotte | 43/122 |
| 3,757,742 | 9/1973 | Schlegel | 119/430 |
| 4,121,372 | 10/1978 | Landaus | 43/122 |
| 4,198,782 | 4/1980 | Kydonieus et al. | 47/58 |
| 4,244,135 | 1/1981 | Harwoods | 43/122 |
| 4,400,903 | 8/1983 | Seidenberger | 43/122 |
| 4,481,216 | 11/1984 | Hubbard et al. | 424/300 |
| 4,657,926 | 4/1987 | Pickett et al. | 514/467 |
| 4,718,193 | 1/1988 | Rosselli | 43/122 |
| 4,780,479 | 10/1988 | Pickett et al. | 514/467 |
| 4,794,724 | 1/1989 | Peters | 43/122 |
| 4,851,218 | 7/1989 | Hildebrandt et al. | 424/84 |
| 4,880,624 | 11/1989 | Metcalf et al. | 424/84 |
| 4,885,177 | 12/1989 | Wegman | 424/95 |
| 4,908,388 | 3/1990 | Pickett et al. | 514/716 |
| 4,930,251 | 6/1990 | Crisanti | 43/107 |
| 4,981,981 | 1/1991 | Aldrich et al. | 549/546 |
| 4,983,390 | 1/1991 | Levy | 424/404 |
| 5,011,683 | 4/1991 | Bartelt et al. | 424/84 |
| 5,057,316 | 10/1991 | Gunner et al. | 424/93 |
| 5,133,150 | 7/1992 | Briese | 43/122 |
| 5,141,744 | 8/1992 | Chang et al. | 424/93 |
| 5,149,525 | 9/1992 | Dowd et al. | 424/84 |
| 5,167,955 | 12/1992 | Teale et al. | 424/84 |
| 5,231,791 | 8/1993 | Falkson | 43/122 |
| 5,231,792 | 8/1993 | Warner | 43/122 |
| 5,392,560 | 2/1995 | Donahue et al. | 43/122 |
| 5,406,743 | 4/1995 | McSherry et al. | 43/122 |
| 5,407,454 | 4/1995 | Cavalieri et al. | 47/58 |
| 5,464,618 | 11/1995 | Doane et al. | 424/195.1 |
| 5,504,142 | 4/1996 | Caupin et al. | 524/548 |
| 5,522,171 | 6/1996 | Mandeville | 43/122 |
| 5,558,862 | 9/1996 | Corbin et al. | 424/94.4 |
| 5,571,522 | 11/1996 | Munson et al. | 424/410 |
| 5,577,344 | 11/1996 | Zaremba et al. | 47/39 |
| 5,596,833 | 1/1997 | Harrie et al. | 43/122 |
| 5,632,987 | 5/1997 | Payne et al. | 424/93.461 |
| 5,682,706 | 11/1997 | Altenberg | 43/122 |
| 5,707,638 | 1/1998 | Losel et al. | 424/407 |
| 5,750,129 | 5/1998 | Wakarchuk | 424/408 |
| 5,759,561 | 6/1998 | Angst et al. | 424/407 |
| 5,799,436 | 9/1998 | Nolen et al. | 43/112 |
| 5,842,305 | 12/1998 | Liao | 43/122 |

*Primary Examiner*—Michael J. Carone
*Assistant Examiner*—Fredrick T. French, III
*Attorney, Agent, or Firm*—Hana Verny

[57] ABSTRACT

A corn rootworm/kairomone insect trap for capturing corn rootworm and other similar insects. A corn rootworm/kairomone trap comprises a capture top dome, a capture reservoir and a container containing a kairomone lure or bait. The trap is useful for corn, peanuts and leafy vegetables crop protection from corn rootworm or other insects.

14 Claims, 3 Drawing Sheets

KAIROMONE INSECT TRAP FOR CAPTURE OF CORN ROOTWORM

This application is based on the provisional application Ser. No. 60/041,305 filed on Mar. 19, 1997.

BACKGROUND OF THE INVENTION

1. Field of the Invention

This invention concerns a kairomone insect trap for capturing corn rootworm and other similar insects. The trap comprises a capture top dome, a capture reservoir and a container containing a kairomone lure or bait to lure the insects to the trap. The trap is useful for monitoring Diabrotica and other insects in corn, peanuts and leafy vegetables crop protection from corn rootworm.

2. Background of the Invention

Corn rootworm poses a serious economic problems for corn crop. Twenty-one million acres of corn are treated annually in many mid-western states with a soil-applied preventative insecticides for controlling western and/or Northern corn rootworm. United States Department of Agriculture (USDA) estimates that only 30% of these applications are justified against economic loss. Moreover, fewer applications are successful for a variety of reasons ranging from poor application to resistance. Thousand of additional acres of corn, peanuts and leafy vegetables are attacked by two other rootworm species, the Southern and Mexican rootworm.

Iowa State University and the USDA have correlated adult capture rates from yellow glue coated cards to plant counts of adults and these have been correlated to larval root pruning damage in corn. This correlation allows for reduced field monitoring time by consultants or pest control advisors and ultimately results in high accuracy of insect population predictions.

However, due mainly to inconvenience in their use, the yellow glue coated cards have been poorly received and were never adopted in any practical way.

It would therefore be important and advantageous to have available a convenient and practical corn rootworm trap having specific means to attract and capture the insect.

Many methods for prevention of insect infestation and crop destruction of corn, peanuts and leafy vegetables were recently devised. The methods for controlling corn rootworm may include treatments with pathogens, the use of various chemicals and insect growth regulators and recently developed insect sex pheromones and other behavior modifying semiochemicals. Various insect traps have been devised which lure the insects, poison the insects, suffocate the insects and/or remove insects from the stored products using any of the above means.

The current invention provides a corn rootworm trap comprising novel features making it extraordinarily practical and effective.

SUMMARY

One aspect of the current invention concerns a kairomone insect trap for capturing corn rootworm and other similar insects.

Another aspect of the current invention concerns an insect trap comprises a capture top dome, a capture reservoir and a container containing a kairomone lure or bait to lure the insects to the trap.

Another aspect of the invention concerns a trap comprising a kill bait.

DETAILED DESCRIPTION OF THE INVENTION

The current invention provides a new type two piece corn rootworm (CRW) trap. The trap comprises a capture top dome, a capture receptacle and a lure or bait to lure the insects to the trap. The lure is typically a kairomone-based attractant. The trap is useful for capturing corn rootworm and similar insects attacking a corn, peanuts and leafy vegetables crop.

Corn rootworm (CRW) trap design features attachments for two types of lures. A kairomone based attractant provides full-season, long-range attraction for CRW adults to the trap surface. The adult corn rootworm land on the trap and find their way up and under the dome cover. As the rootworms enter the area under the dome, they are lured to a full season feeding stimuli mixed with a small amount of insecticide toxicant and are killed within a short time. They then fall into a reservoir which can be removed for counting insects, cleaning the trap and replacing baits if necessary. The clear plastic-based design allows for multiple season use after replacement of lures and allows the user to see insect trapped inside.

The corn rootworm trap features state of the art design characteristics. The design considers insect behavioral preference, such as weather conditions, lure attractiveness, longevity and placement, trap placement, efficiency of data collection, user appeal and production cost.

The trap of the invention allows users detect, monitor emergence and to accurately decide on treating corn rootworm populations based on the number and sex ratio of adults captured in the trap to allow for adult treatment only when necessary versus preventative treatments with soil applied insecticides. The new trap leads to substantial reduction in the annual environmental pesticide load.

Kairomone Corn Rootworm Trap

Figure 1:
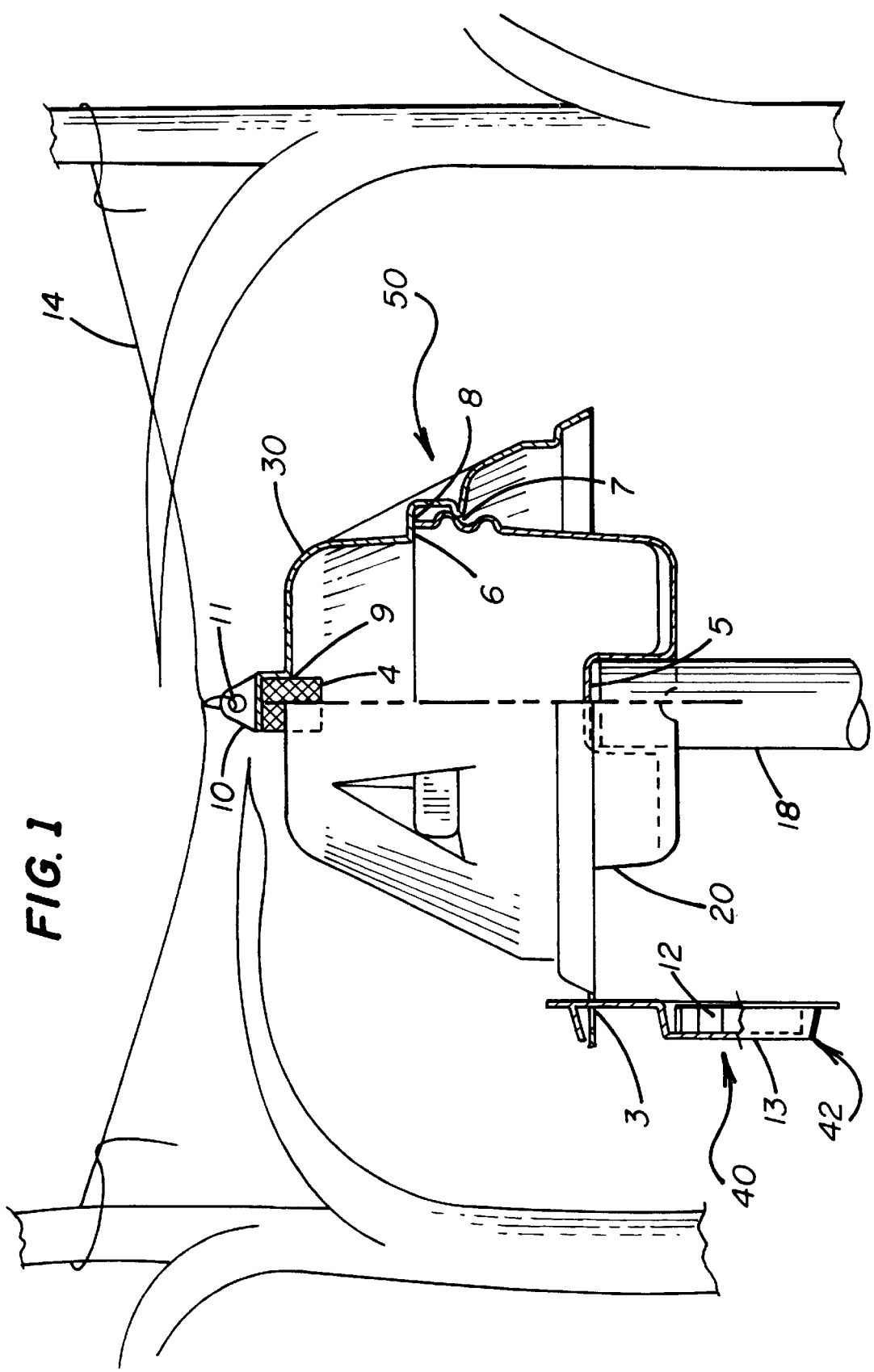
FIG. 1 is a side view of an assembled corn rootworm trap.
Figure 2:
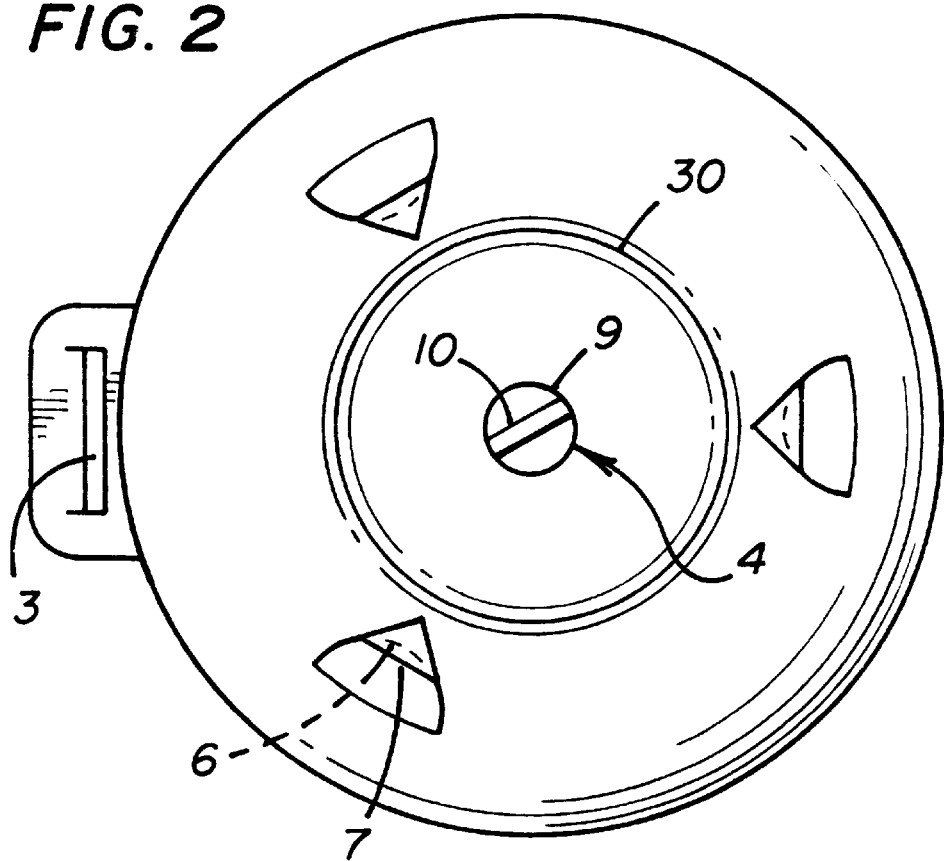
FIG. 2 is a upside view of a trap capture top dome.
Figure 3B:
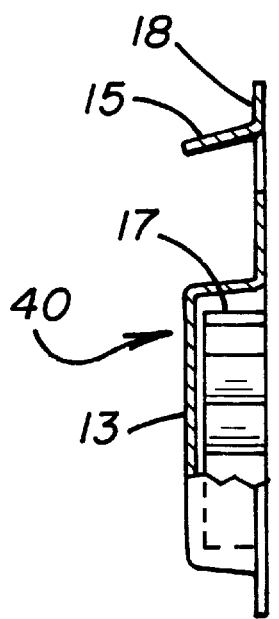
FIG. 3 is a corn rootworm kairomone lure dispenser, front view (FIG. 3A), side view (FIG. 3B).
Figure 3A:
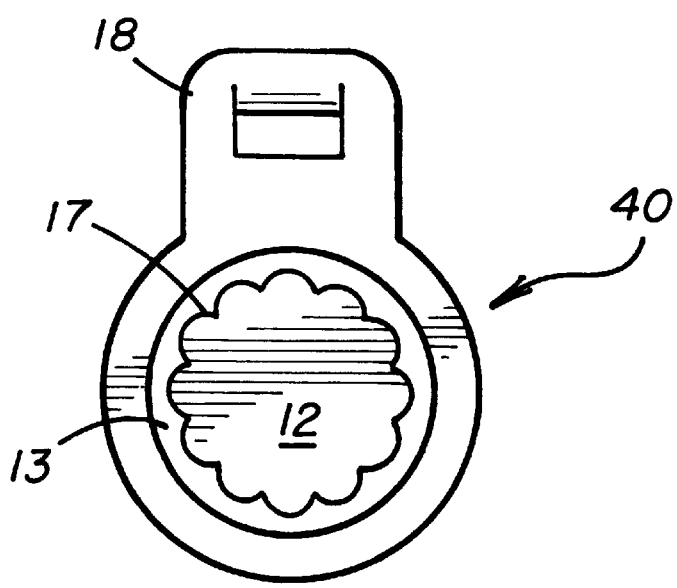

Kairomone corn rootworm trap and its three major components are shown in FIGS. 1–3.

FIG. 1 shows a two piece corn rootworm trap made of clear polyethylene (PET) or polyvinylchloride (PVC) allowing user to see insects trapped inside.

Trap 50 consists of trap dome or top dome 30 containing a kill bait 4, kill bait insertion slot 9, hanging attachments 10 and 11, retaining stop 6, locking tab 7 for the catch receptacle, reservoir or container 20 which controls size of the opening 8 and serves to lock the two pieces 20 and 30 of the trap 50 together. Trap catch container or capture reservoir 20 shows female part of locking device 7 and a hole 5 allowing insertion of field stake 18. The sides of both parts 20 and 30 are angled to various degree for maximum efficiency of trap entry by rootworm adults or sides of the top dome may be straight. The bottom or capture container 20 easily snaps into the top dome 30 of the trap and can be easily opened for inspection. The Kairomone lure holder is inserted into female insertion of slot 3. Kill bait 4 typically consists of a pill containing a mixture of cucurbitacin feeding stimuli with a carbaryl insecticide bound together by a special formulation of paraffin, such as 60% by volume of paraffin of a melting point above 160 degrees F. Insert hole or slot 5 for insertion of field stake is made from ⅜ inch PVC irrigation pipe to be used as an alternative to the top hanging device for low growing crops. Stop tab 6 for the capture reservoir prevents closing of the circular opening between the two trap pieces 20 and 30. This part insures uniformity of the opening which lowers variation in trap capture. There are several, typically three or four locking tabs 7 insuring attachment of the capture reservoir 20 to the trap top or dome 30. Locking tab extension is smooth in curvature with a depth of under ⅛ inch. Depths over this amount severely reduce capture rate since the insect shows an aversion to crawling over the area. Opening 8 between the trap top or dome 30 and the capture reservoir 20 must be maintained at a uniform distance.

Kill bait insertion hole or slot 9 is tapered to insure a friction fit of the kill bait pill. Top of attachment hanger tap 10 is an integral piece of the teat used internally as the kill bait holder. There is no opening from the inside of the trap to the outside as a result of this. This is an important feature insuring that there is no interference with attraction outside the opening 8. Top hanger insert hole of attachment 11 is for hanging a plastic coated wire hanger or any other hanging or attachment means.

Kairomone lure 40 holder 42 has a laminated seal 12 which seals the Kairomone lure holder. The seal 12 consists of an inner layer of BAREX™ plastic and an outer layer of foil. BAREX™ 13 is used for the plastic Kairomone lure container. The barex is a necessary nonpermeable barrier extending the shelf life and otherwise protecting the content, that is the lure, from the environmental elements and in reverse, the user from the content of the lure. Plastic wire hanger 15 or other hanging means allows exact placement of trap between tall growing crops like corn or for hanging in fields from stakes.

Kairomone lure container lock-back tap 15 to prevent container from falling out of female insertion slot. Kairomone lure container male insertion tab 16 fitting into female insertion slot. Kairomone lure dispenser 17 is made of high void, highly absorbent polyethylene. The dispenser absorbs a high rate of the active ingredients, release them slowly and protect them from the environment. Alternative suspension means is PVC pipe 18 inserted into the hole 5.

FIG. 2 shows the top dome from the bottom view and shows a locking tabs 7 as well as stop tabs 6. Also seen is the insertion hole 9 for insertion of the kill bait 4 and the female insertion slot 3 for insertion of the kairomone holder and male insertion tab 16.

FIG. 3 shows a kairomone lure holder in the front and side views. Kairomone lure container male insertion tab 16 prevents container from falling out of the female insertion slot.

FIG. 1 illustrates the preferred embodiment of the current invention. Variations of the trap in size, material used or shape are intended to be within a scope of the invention.

The trap is made of light but durable plastic which is preferably transparent to allow the monitor to see how many insects are inside and/or to empty or change the the bottom receptacle section 20. The bottom receptacle is easily removable, emptiable or exchangeable. Thus when the trap becomes too full, the bottom receptacle 20 can be removed and emptied or exchanged. This feature is important particularly for monitoring the number of insects and/or degree of infestation when the receptacle may be, for example, exchanged or checked on a daily, weekly or monthly basis to provide information on whether or not there is an infestation and what the degree of the infestation is. The primary fucntion of the trap is, of course, a capture of the insect to detect and monitor leading elimination of the infestation.

The trap size, material and shape allows the use of the trap anywhere regardless of the environment or weather. It is made of completely non-toxic molded plastic material. There is no known insect which would eat and digest the plastic material. The material is safe to be used even in instances where the trap is placed inside. Moreover, the used plastic is reasonably hard so that it is break-proof and does not deteriorate or disintegrate in humid, dry, hot or cold weather.

Since the various specific kairomones and feeding stimuli may be selected, supplied and or used and exchanged for different insects, the current trap is very versatile, practical and economical.

The feeding stimuli may be any chemical compound or food which will attract the insectsuch as plant or oil-based food attractant, and it may be used alone or it may be a mixture of two or more compounds, for example, it may be a mixture of the food and insecticide. The mixture of both would then be used to attract and kill the insect.

The new trap is more efficient in capturing male and female insects than other existing traps over the full season.

The Kairomone lure is selected from the group of compounds identifed as 1,2,4-trimethoxybenzene, indole, trans-cinnamaldehyde, eugenol, 4-methoxyphenethanol and 4-methoxy cinnamaldehyde alone or in a mixture as seen in Table 1.

TABLE 1

CRW Lures
TRE Designations

| Lure Number | Substrate | 1,2,4-Trimethoxybenzene | Indole | trans-Cinnamaldehyde | Eugenol | 4-Methoxyphenethanol | 4-Methoxy Cinnamaldehyde |
|---|---|---|---|---|---|---|---|
| TRE 8274 | GP-202 H.V. | 250 mg | 250 mg | 250 mg | | | 750 mg |
| TRE 8275 | GP-202 H.V. | | | | | | 1500 mg |
| TRE 8276 | GP-202 H.V. | 500 mg | 500 mg | 500 mg | | | |
| TRE 8279 | GP-202 H.V. | | | | 1500 mg | | |
| TRE 8280 | GP-202 H.V. | | | 1500 mg | | | |
| TRE 8281 | GP-202 H.V. | | | | | 1500 mg | |
| TRE 8282 | GP-202 H.V. | | | | | 750 mg | 750 mg |
| TRE 8291-1 | GP-202 H.V. | | 500 mg | 500 mg | 500 mg | | |

TABLE 1-continued

CRW Lures
TRE Designations

| Lure Number | Substrate | 1,2,4-Trimethoxybenzene | Indole | trans-Cinnamaldehyde | Eugenol | 4-Methoxyphenethanol | 4-Methoxy Cinnamaldehyde |
|---|---|---|---|---|---|---|---|
| TRE 8291-T | GP-202 H.V. | 500 mg | | 500 mg | 500 mg | | |
| TRE 8292 | GP-202 H.V. | 375 mg | 375 mg | 375 mg | 375 mg | | |
| TRE 8326 | GP-202 H.V. | | | 750 mg | 750 mg | | |
| TRE 8331 | GP-202 H.V. | | | 750 mg | 750 mg | | |
| TRE 8336 | GP-202 H.V. | 500 mg | | 500 mg | | 500 mg | |
| TRE 8337 | GP-202 H.V. | | | | 750 mg | 375 mg | 375 mg |
| TRE 8336 | GP-202 H.V. | 250 mg | 250 mg | 250 mg | | | |
| TRE 8339 | ½ GP-202 H.V. | 500 mg | 500 mg | 500 mg | | | |
| TRE 8340 | ½ GP-202 H.V. | 250 mg | 250 mg | 250 mg | | | |
| TRE 8341 | GP-203 BRG-100 | 500 mg | 500 mg | 500 mg | | | |
| TRG 8342 | GP-203 BRG-100 | 250 mg | 250 mg | 250 mg | | | |
| TRE 8343 | FOAM | 500 mg | 500 mg | 500 mg | | | |
| TRE 8344 | FOAM | 250 mg | 250 mg | 250 mg | | | |
| TRE 8345 | . . . POLY ROD | 500 mg | 500 mg | 500 mg | | | |
| TRE 8346 | POLY ROD | 250 mg | 250 mg | 250 mg | | | |

The effectivity of the CRW trap of the invention has been tested in various conditions and compared to the effectivity of the other types of traps. The results are summarized in enclosed Tables of the actual field trials performed during and off season.

The following examples illustrate testing conditions and results of the trap testing against various insects.

Field Testing of the CRW Kairomone Trap

1. Corn Rootworm Trapping Studies

Corn rootworm trapping studies were conducted on the Texas High Plains in summer 1997. These field tests had three major objectives: (1) compare the timing and numbers of emerging western and Mexican corn rootworm. (2) compare three types of traps for monitoring CRW emergence, and (3) compare two types of the CRW lures aged for different periods of time.

These field evaluations were conducted in five irrigated corn fields in the Northern High Plains of Texas. Fields 1 and 2 were in Parmer County, fields 4 and 5 were in Castro County, and field 3 was in Swisher County. For the bait comparison, only field 1 was used. Each bait type was placed down a row approximately 75 meters apart. The test was replicated five times with each replicate being 25 rows apart.

For evaluation for corn rootworm emergence, sticky traps (FIG. 6), CRW traps (FIG. 6) baited with 8276 lures, and emergence traps (modified pecan weevil traps) were used. The different types of traps were randomized approximately 75 meters down rows of corn. Each treatment was replicated five times, 25 rows apart, at each of the five test fields. The traps were deployed and were serviced weekly except for the last time which was 11 days. At each sampling date, ten plants were sampled per replicate with a "Corn Kiss Sampler". This sampler used a leaf blower to blow 180 mph airstream across the corn plant into a sampling net.

In the bait comparison, the CRW bait 8276 deployed for the length of the test, changed weekly, and aged ten days prior to the start of the test, were all about equal in the effectiveness against both the western and Mexican corn rootworm (Tables 2 and 3). The most effective bait for both types of CRW was the bait 8337, changed weekly.

The results from these studies did not show a significant time difference in the emergence of Mexican and western corn rootworm (Tables 2 and 3). The CRW population in the three county area was 90–95% Western and 5–10% Mexican. The emergence of both types of CRW was somewhat extended since capturing adults began the day the traps were deployed and continued to catch them until were removed. Emerging adult CRW were captured over a 45-period. The extended emergence may have been related to the cool, wet weather which prevailed in the area.

TABLE 2

Numbers of Western Corn Rootworm Captured per Observation Period
Average number WCR per trap per observation period.

| | July 8 | July 15 | July 22 | July 28 | Aug 5 | Aug 16 | Total |
|---|---|---|---|---|---|---|---|
| Parmer Co. TX Field 1 Bait Tests | | | | | | | |
| Emergence cage | 1.8 | 1.2 | 2.6 | 0.4 | 0.4 | 2 | 8.4 |
| Sticky trap | 31.0 | 12.8 | 14.0 | 12.2 | 12.8 | 7.8 | 90.6 |
| Trece crw trap/8276 lure | 100.8 | 10.6 | 33.6 | 95.8 | 121.6 | 166.6 | 529 |
| Trece crw trap/lure 8276 aged 10 days | 62.4 | 16.2 | 42.2 | 129.8 | 179.8 | 151.4 | 581.8 |
| Trece crw trap/lure 8276 changed weekly | 74.4 | 18.6 | 42.2 | 142.8 | 206.6 | 175.8 | 660.4 |
| Trece crw trap/lure 8337 | 62.4 | 21.2 | 44.8 | 118.4 | 98.0 | 114.4 | 459.2 |
| Trece crw trap/lure 8337 changed weekly | 88.4 | 37.4 | 88.2 | 288.6 | 246.4 | 303.2 | 1052.2 |
| KISS # WCR/plant | 0.54 | 3.0 | 1.26 | 0.56 | 0.08 | 0.0 | 5.44 |

TABLE 2-continued

Numbers of Western Corn Rootworm Captured per Observation Period
Average number WCR per trap per observation period.

|  | July 8 | July 15 | July 22 | July 28 | Aug 5 | Aug 16 | Total |
| --- | --- | --- | --- | --- | --- | --- | --- |
| Parmer Co. Field 2 | | | | | | | |
| Emergence cage | 0 | 1.8 | 2.8 | 2.2 | 0.2 | 0 | 7 |
| Sticky trap | 4 | 12 | 15.4 | 28 | 12.6 | 0.6 | 72.6 |
| Trece crw trap/8276 lure | 0 | 37.4 | 96.4 | 149.8 | 417.4 | 15.6 | 716.6 |
| KISS # WCR/plant | 0.26 | 1.48 | 1.1 | 1.04 | 0.04 | 0 | 3.92 |
| Swisher Co. Field 3 | | | | | | | |
| Emergence cage | 0.8 | 0.6 | 0 | 0 | 0 | 0 | 1.4 |
| Sticky trap | 4.8 | 1.2 | 3.6 | 2 | 2.8 | 1 | 15.4 |
| Trece crw trap/8276 lure | 11.6 | 13.6 | 46.2 | 5.2 | 4.6 | 4.8 | 86 |
| KISS # WCR/plant | 0.26 | 1.46 | 0.12 | 0.22 | 0.2 | 0 | 2.26 |
| Castro Co. Field 4 | | | | | | | |
| Emergence cage | 3 | 5.6 | 0.4 | 0.2 | 0 | 0 | 9.2 |
| Sticky trap | 7.4 | 37 | 22 | 8.4 | 5.4 | 0.6 | 80.8 |
| Trece crw trap/8276 lure | 17.6 | 87.75 | 19 | 8.4 | 38 | 9.8 | 163 |
| KISS # WCR/plant | 0.1 | 0.82 | 0.26 | 0.08 | 0.08 | 0 | 1.34 |
| Castro Co. Field 5 | | | | | | | |
| Emergence cage | 1 | 3.2 | 4.2 | 2 | 0.2 | 0 | 10.6 |
| Sticky trap | 2.4 | 19.4 | 12 | 9.8 | 6.8 | 9 | 59.4 |
| Trece crw trap/8276 lure | 9.2 | 8.6 | 12.6 | 24.8 | 71 | 76.4 | 202.6 |
| KISS # WCR/plant | 0.26 | 2.24 | 0.52 | 0.68 | 0.34 | 0 | 4.04 |

TABLE 3

Numbers of Mexican Corn Rootworm Captured per Observation Period
Average number MCR per trap per observation period.

|  | July 8 | July 15 | July 22 | July 28 | Aug 5 | Aug 16 | Total |
| --- | --- | --- | --- | --- | --- | --- | --- |
| Parmer Co. Field 1 Bait Tests | | | | | | | |
| Emergence cage | 0.4 | 0 | 0.8 | 0 | 0.4 | 0.2 | 1.8 |
| Sticky trap | 1 | 0.2 | 1.4 | 1 | 0.6 | 0.2 | 4.4 |
| Trece crw trap/8276 lure | 3.4 | 1 | 3.4 | 4.4 | 4.2 | 5.4 | 21.8 |
| Trece crw trap/lure 8276 aged 10 days | 4.2 | 0.8 | 1.8 | 5.6 | 2.8 | 4.2 | 19.4 |
| Trece crw trap/lure 8276 changed weekly | 1.6 | 0.2 | 4 | 7.4 | 4.4 | 5 | 22.6 |
| Trece crw trap/lure 8337 | 6.6 | 0.6 | 4 | 4.2 | 3 | 3.8 | 22.2 |
| Trece crw trap/lure 8337 changed weekly | 3.4 | 0.4 | 22 | 10 | 6 | 9.4 | 36 |
| KISS # WCR/plant | 0 | 0.4 | 0.16 | 0 | 0.04 | 0 | 0.56 |
| Parmer Co. Field 2 | | | | | | | |
| Emergence cage | 0 | 0.6 | 0.4 | 0 | 0.2 | 0 | 1 |
| Sticky trap | 0 | 0 | 0.2 | 1.8 | 0.2 | 0.4 | 2.6 |
| Trece crw trap/8276 lure | 0 | 7.4 | 6.8 | 3.8 | 5.8 | 0.6 | 24.4 |
| KISS # WCR/plant | 0 | 0.2 | 0.1 | 0.16 | 0 | 0 | 0.46 |
| Swisher Co. Field 3 | | | | | | | |
| Emergence cage | 0 | 0.2 | 0 | 0 | 0 | 0 | 0.2 |
| Sticky trap | 0 | 0.6 | 0 | 0.2 | 0 | 0 | 0.8 |
| Trece crw trap/8276 lure | 0.2 | 9 | 4.2 | 0.2 | 0.6 | 0.4 | 14.6 |
| KISS # WCR/plant | 0 | 0.26 | 0.04 | 0.06 | 0 | 0 | 0.36 |
| Castro Co. Field 4 | | | | | | | |
| Emergence cage | 1.2 | 0.8 | 0 | 0.2 | 0 | 0 | 2.2 |
| Sticky trap | 1.8 | 7.6 | 1.8 | 1 | 0.2 | 0.2 | 12.6 |
| Trece crw trap/8276 lure | 1.6 | 12.25 | 0.6 | 1 | 1.4 | 0.6 | 15 |
| KISS # WCR/plant | 0 | 0.34 | 0.06 | 0.06 | 0.02 | 0 | 0.48 |
| Castro Co. Field 5 | | | | | | | |
| Emergence cage | 1.4 | 0.4 | 1.4 | 0.8 | 0 | 0 | 4 |
| Sticky trap | 0.4 | 2 | 0.2 | 0.2 | 0.4 | 0.4 | 3.6 |
| Trece crw trap/8276 lure | 2.4 | 4 | 2.6 | 1.4 | 3.4 | 3.6 | 17.4 |
| KISS # WCR/plant | 0 | 0.14 | 0.12 | 0.1 | 0.04 | 0 | 0.4 |

2. Lure and Trap Comparison

The research results for the lure and trap comparison tests for both the western (w) and southern (s) corn rootworms. These tests were conducted at Scandia, Kans. within the Rootworm Areawide Project's "treated" area, however this field did not reach the treatment threshold. The rootworm populations, both species, were adequate to discern differences.

A. Lure Test for Western Corn Rootworm

In order to compare various lure formulations of corn rootworm (CRW) kairomone for optimum results against western and southern CRW, the field finals were run by the Kansas State University. The trials compared various sticky and non-sticky kairomone based trap designs for efficacy.

Four replicates of eleven different formulations were tested and changed at four week intervals. Traps were observed, counted and emptied at seven day intervals, data recorded and entered. Traps were placed at a density of 60 feet of row. Kill bait was changed only when necessary.

Various trap designs and/or refinements were tested using sticky traps or kairomone type traps. Non-baited dull sticky traps were replicated four times. Kairomone lures were changed twice per season. Traps were observed and counted at seven day intervals.

Treatments with coding:

Baited Dull Sticky Trap (BDST)
Baited Bright Sticky Trap (BTBS)
Clear Top White Bottom Trece Kairomone Trap (CTWB)
Clear Top Yellow Bottom Trece Pheromone Trap (CYTB)
Clear Top Clear Bottom Trece Pheromone Trap (CTCB)
Non-Baited Bright Sticky Trap (NBBS)
Sutter Type Old Style Kairomone Trap (SUTT)
Alpha=0.05 df=56 MSE=228.0468
Critical Vaulue of T=2.00
Least Significant Difference=16.7
WARNING: Cell sizes are not equal.
Harmonic Mean cf cell sizes=6.5625
Means with the same letter are not significantly different.

| T Grouping | | Mean | N | LURE |
|---|---|---|---|---|
| A | | 63.333 | 6 | 8391 |
| B | | 33.857 | 7 | 8337 |
| C | | 13.000 | 6 | 8276 |
| C | | | | |
| C | | 6.143 | 7 | 8326 |
| C | | | | |
| C | | 5.286 | 7 | 8280 |
| C | | | | |
| C | | 4.857 | 7 | 8279 |
| C | | | | |
| C | | 3.286 | 7 | 8336 |
| C | | | | |
| C | | 3.000 | 7 | 8291-T |
| C | | | | |
| C | | 2.857 | 7 | 8347 |
| C | | | | |
| C | | 1.857 | 7 | 8281 |
| C | | | | |
| C | | 0.800 | 5 | 8390 |

Alpha=0.05 df=20 MSE=10321.78
Critical Value of T=2.09
Least Significant Difference=123.23
WARNING: Cell sizes are not equal.
Harmonic Mean of cell sizes=5.915493
Means with the same letter are not significantly different.

| T Grouping | | Mean | N | LURE |
|---|---|---|---|---|
| | A | 265.43 | 7 | 8391 |
| | A | | | |
| B | A | 156.71 | 7 | 8337 |
| B | | | | |
| B | C | 125.50 | 4 | 8276 |
| | C | 11.67 | 6 | 8336 |
| | C | | | |
| | C | 11.57 | 7 | 8326 |

Alpha=0.05 df=57 MSE=2586.34
Critical Value of T=2.00
Least Significant Difference=59.145
WARNING: Cell sizes are not equal.
Harmonic Mean of cell sizes=5.929412
Means with the same letter are not significantly different.

| T Grouping | Mean | N | LURE |
|---|---|---|---|
| A | 204.29 | 7 | 8391 |
| B | 139.43 | 7 | 8337 |
| B | | | |
| B | 112.67 | 6 | 8276 |
| B | | | |
| B | 91.67 | 3 | 6282 |
| C | 11.67 | 6 | 8336 |
| C | | | |
| C | 11.57 | 7 | 8326 |
| C | | | |
| C | 9.33 | 6 | 8280 |
| C | | | |
| C | 8.50 | 6 | 8291-T |
| C | | | |
| C | 7.43 | 7 | 8281 |
| C | | | |
| C | 6.57 | 7 | 8347 |
| C | | | |
| C | 3.50 | 6 | 8390 |
| C | | | |
| C | 3.29 | 7 | 8279 |

Alpha=0.05 df=38 MSE=2991.499
Critical Value of T=2.02
Least Significant Difference=82.322
WARNING: Cell sizes are not equal.
Harmonic Mean of cell sizes=3.61809
Means with the same letter are not significantly different.

| T Grouping | | | Mean | N | LURE |
|---|---|---|---|---|---|
| | | A | 352.67 | 3 | 8391 |
| | | B | 113.33 | 6 | 8337 |
| | | B | | | |
| | C | B | 74.00 | 1 | 8282 |
| | C | B | | | |
| | C | B | 35.83 | 6 | 8347 |
| | C | B | | | |
| | C | B | 31.17 | 6 | 8276 |
| | C | | | | |
| | C | | 12.60 | 5 | 8336 |
| | C | | | | |
| | C | | 11.17 | 6 | 8326 |
| | C | | | | |

-continued

| T Grouping | Mean | N | LURE |
|---|---|---|---|
| C | 9.50 | 4 | 8291-T |
| C | | | |
| C | 8.40 | 5 | 8390 |
| C | | | |
| C | 6.67 | 6 | 8280 |
| C | | | |
| C | 5.00 | 4 | 6281 |
| C | | | |
| C | 2.75 | 4 | 8279 |

Alpha=0.05 df=25 MSE=176.8757
Critical Value of T=2.06
Least Significant Difference=21.75
WARNING: Cell sizes are not equal.
Harmonic Mean of cell sizes=3.171806
Means with the same letter are not significantly different.

| T Grouping | Mean | N | LURE |
|---|---|---|---|
| A | 137.00 | 4 | 8391 |
| B | 66.67 | 3 | 8337 |
| C | 42.00 | 3 | 8276 |
| C | | | |
| C | 38.00 | 3 | 8282 |
| D | 13.50 | 4 | 8336 |
| D | | | |
| D | 12.25 | 4 | 8326 |
| D | | | |
| D | 11.50 | 4 | 8280 |
| D | | | |
| D | 10.50 | 2 | 8347 |
| D | | | |
| D | 9.00 | 4 | 8291-T |
| D | | | |
| D | 5.00 | 2 | 8279 |
| D | | | |
| D | 3.80 | 5 | 8281 |
| D | | | |
| D | 2.00 | 3 | 8390 |

Alpha=0.05 df=56 MSE=208.6729
Critical Value of T=2.00
Least Significant Difference=19.292
WARNING: Cell sizes are not equal.
Harmonic Mean of cell sizes=4.5
Means with the same letter are not significantly different.

| T Grouping | | | Mean | N | LURE |
|---|---|---|---|---|---|
| | | A | 54.286 | 7 | 8391 |
| | | A | | | |
| B | | A | 38.167 | 6 | 8337 |
| B | | | | | |
| B | | | 32.143 | 7 | 8276 |
| | | C | 8.143 | 7 | 8336 |
| | | C | | | |
| | | C | 6.143 | 7 | 8291-T |
| | | C | | | |
| | | C | 5.667 | 6 | 8347 |
| | | C | | | |
| | | C | 4.167 | 6 | 8326 |
| | | C | | | |
| | | C | 3.167 | 6 | 8280 |
| | | C | | | |
| | | C | 3.143 | 7 | 8390 |
| | | C | | | |
| | | C | 3.000 | 1 | 8282 |
| | | C | | | |

| T Grouping | Mean | N | LURE |
|---|---|---|---|
| C | 2.143 | 7 | 8281 |
| C | | | |
| C | 0.429 | 7 | 8279 |

Alpha=0.05 df=53 MSE=20.65901
Critical Value of T=2.01
Least Significant Difference=6.1799
WARNING: Cell sizes are not equal.
Harmonic Mean of cell sizes=4.352332
Means with the same letter are not significantly different.

| T Grouping | Mean | N | LURE |
|---|---|---|---|
| A | 20.800 | 5 | 8391 |
| B | 12.333 | 6 | 8337 |
| B | | | |
| B | 9.429 | 7 | 8276 |
| C | 3.143 | 7 | 8347 |
| C | | | |
| C | 3.000 | 5 | 8390 |
| C | | | |
| C | 2.833 | 6 | 8336 |
| C | | | |
| C | 2.286 | 7 | 8291-T |
| C | | | |
| C | 1.714 | 7 | 8281 |
| C | | | |
| C | 0.857 | 7 | 8326 |
| C | | | |
| C | 0.714 | 7 | 8280 |
| C | | | |
| C | 0.000 | 1 | 8282 |
| C | | | |
| C | 0.000 | 6 | 8279 |

Alpha=0.05 df=56 MSE=2.616641
Critical Value of T=2.00
Least Significant Difference=2.1642
WARNING: Cell sizes are not equal.
Harmonic Mean of cell sizes=4.483986
Means with the same letter are not significantly different.

| T Grouping | | | Mean | N | LURE |
|---|---|---|---|---|---|
| | A | | 4.600 | 5 | 8391 |
| | A | | | | |
| B | A | | 2.571 | 7 | 8337 |
| B | | | | | |
| B | | C | 1.857 | 7 | 6326 |
| B | | C | | | |
| B | | C | 1.429 | 7 | 8276 |
| B | | C | | | |
| B | | C | 1.286 | 7 | 8291-T |
| B | | C | | | |
| B | | C | 1.000 | 1 | 8282 |
| B | | C | | | |
| B | | C | 0.833 | 6 | 8281 |
| B | | C | | | |
| B | | C | 0.571 | 7 | 8336 |
| B | | C | | | |
| B | | C | 0.571 | 7 | 8280 |
| | | C | | | |
| | | C | 0.333 | 6 | 8390 |
| | | C | | | |
| | | C | 0.286 | 7 | 8347 |
| | | C | | | |
| | | C | 0.000 | 7 | 8279 |

Alpha=0.05 df=21 MSE=4.082798
Critical Value of T=2.08
Least Significant Difference=29.713
Means with the same letter are not significantly different.

| T Grouping | | | Mean | N | TRAP |
|---|---|---|---|---|---|
| | A | | 89.75 | 4 | bdsti = baited dull sticky |
| | A | | | | |
| | A | | 89.25 | 4 | btbs = baited bright sticky |
| | B | | 56.00 | 4 | ctwb = clear top white bottom |
| | B | | | | |
| | B | | 53.50 | 4 | ctyb = clear top yellow bottom |
| | B | | | | |
| | B | | 50.75 | 4 | ctcb = clear top clear bottom |
| | B | | | | |
| C | B | | 33.00 | 4 | nbbs = nonbaited bright sticky |
| C | | | | | |
| C | D | | 17.25 | 4 | sutt = sutter |
| | D | | | | |
| | D | | 3.00 | 4 | nbds = nonbaited dull sticky |

Alpha=0.05 df=21 MSE=310.6146
Critical Value of T=2.08
Least Significant Difference=25.917
Means with the same letter are not significantly different.

| T Grouping | | | Mean | N | TRAP |
|---|---|---|---|---|---|
| | A | | 75.50 | 4 | btbs |
| | A | | | | |
| B | A | | 56.25 | 4 | bdst |
| B | | | | | |
| B | C | | 47.75 | 4 | ctcb |
| B | C | | | | |
| B | C | | 42.75 | 4 | ctwb |
| B | C | | | | |
| B | C | | 42.25 | 4 | ctyb |
| B | C | | | | |
| B | C | D | 31.25 | 4 | sutt |
| | C | D | | | |
| | C | D | 29.00 | 4 | nbbs |
| | | D | | | |
| | | D | 8.00 | 4 | nbds |

B. B Trap Test

Alpha=0.05 df=5 MSE=120.1714
Critical Value of T=2.57
Least Significant Difference=30.976
WARNING: Cell sizes are not equal.
Harmonic Mean of cell sizes=1.655172
Means with the same letter are not significantly different.

| T Grouping | | | Mean | N | TRAF |
|---|---|---|---|---|---|
| | A | | 49.00 | 1 | bdst |
| | A | | | | |
| | A | | 48.00 | 1 | btbs |
| | A | | | | |
| B | A | | 33.50 | 2 | ctcb |
| B | A | | | | |
| B | A | C | 24.00 | 3 | ctyb |
| B | A | C | | | |
| B | A | C | 20.00 | 2 | ctwb |
| B | | C | | | |
| B | | C | 14.50 | 2 | sutt |
| B | | C | | | |
| B | | C | 5.00 | 2 | nbbs |
| | | C | | | |
| | | C | 0.00 | 2 | nbds |

Alpha=0.05 df=12 MSE=401.5503
Critical Value of T=2.18
Least Significant Difference=37.811
WARNING: Cell sizes are not equal.
Harmonic Mean of cell sizes=2.666667
Means with the same letter are not significantly different.

| T Grouping | | Mean | N | TRAP |
|---|---|---|---|---|
| | A | 62.00 | 2 | btbs |
| | A | | | |
| B | A | 35.50 | 2 | bdst |
| B | | | | |
| B | | 21.67 | 3 | ctwb |
| B | | | | |
| B | | 21.33 | 3 | ctcb |
| B | | | | |
| B | | 21.33 | 3 | ctyb |
| B | | | | |
| B | | 13.00 | 3 | nbbs |
| B | | | | |
| B | | 6.00 | 3 | sutt |
| B | | | | |
| B | | 2.67 | 3 | nbds |

Alpha=0.05 df=21 MSE=262.0908
Critical Value of T=2.08
Least Significant Difference=23.806
Means with the same letter are not significantly different.

| T Grouping | | | Mean | N | TRAP |
|---|---|---|---|---|---|
| | A | | 64.75 | 4 | btbs |
| | A | | | | |
| B | A | | 46.75 | 4 | bdst |
| B | | | | | |
| B | | C | 35.00 | 4 | ctyb |
| | | C | | | |
| D | | C | 19.75 | 4 | ctcb |
| D | | C | | | |
| D | | C | 18.25 | 4 | ctwb |
| D | | C | | | |
| D | | C | 13.25 | 4 | sutt |
| D | | | | | |
| D | | | 6.50 | 4 | nbbs |
| D | | | | | |
| D | | | 1.50 | 4 | nbds |

Alpha=0.05 df=21 MSE=49.91071
Critical Value of T=2.08
Least Significant Difference=10.389
Means with the same letter are not significantly different.

| T Grouping | | Mean | N | TRAP |
|---|---|---|---|---|
| | A | 16.500 | 4 | btbs |
| | A | | | |
| B | A | 13.000 | 4 | bdst |
| B | A | | | |
| B | A | 11.500 | 4 | ctyb |
| B | A | | | |

-continued

| T Grouping | | | Mean | N | TRAP |
|---|---|---|---|---|---|
| B | A | C | 7.750 | 4 | ctwb |
| B | A | C |  |  |  |
| B | A | C | 7.500 | 4 | ctcb |
| B |  | C |  |  |  |
| B |  | C | 3.500 | 4 | sutt |
| B |  | C |  |  |  |
| B |  | C | 2.750 | 4 | nbbs |
|  |  | C |  |  |  |
|  |  | C | 1.000 | 4 | nbds |

Alpha=0.05 df=20 MSE=10.32381
Critical Value of T=2.09
Least Significant Difference=4.837
WARNING: Cell sizes are not equal.
Harmonic Mean of cell sizes=3.84
Means with the same letter are not significantly different.

| T Grouping | Mean | N | TRAP |
|---|---|---|---|
| A | 4.500 | 4 | btbs |
| A |  |  |  |
| A | 4.000 | 4 | nbbs |
| A |  |  |  |
| A | 2.000 | 3 | ctcb |
| A |  |  |  |
| A | 1.500 | 4 | ctyb |
| A |  |  |  |
| A | 1.250 | 4 | bdst |
| A |  |  |  |
| A | 0.750 | 4 | ctwb |
| A |  |  |  |
| A | 0.750 | 4 | sutt |
| A |  |  |  |
| A | 0.000 | 4 | nbds |

3. Southern Corn Rootworm Trapping Program

Figure 4:
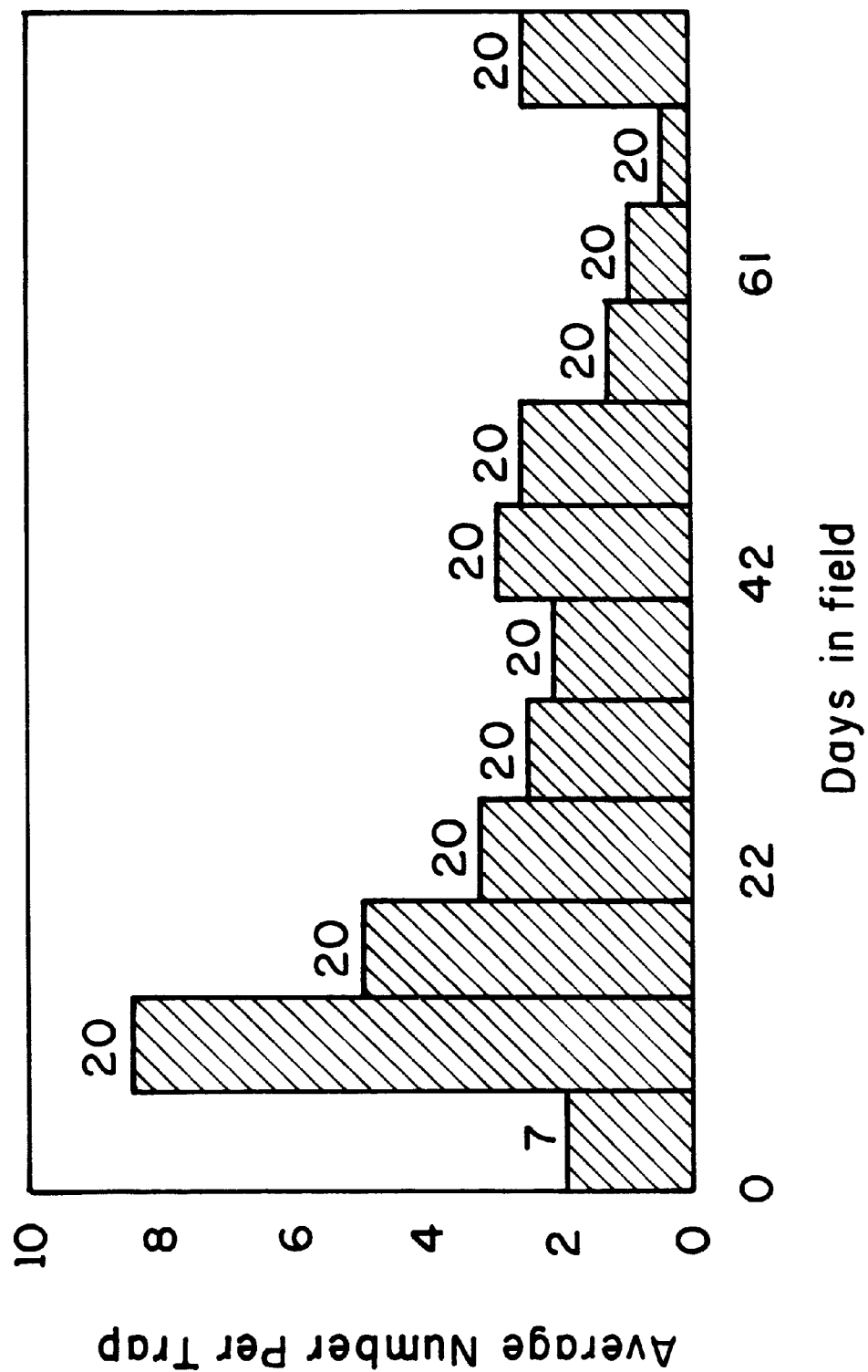
FIG. 4 shows results of trap catches of Southern corn rootworm during the season from July to September.

The field testing of trap catching was performed in Gaines County in Texas. Results are seen in FIG. 4 which illustrates Southern corn rootworm trapping from July to September. FIG. 4 shows three adult insect peaks during the tested season, which corresponded well with measured larval activity observed afterwards in the peanuts fields.

|  | Trap | Net | Ground |
|---|---|---|---|
| Average No. 15 |  |  |  |
| No. Days 7 |  |  |  |
| N | 6 | 1 | 0 |
| S | 10 | 0 | 0 |
| E | 16 | 0 | 0 |
| W | 11 | 0 | 0 |
| CP | 32 | 0 | 0 |
| Total | 75 | 1 | 0 |
| Average No. 4.2 |  |  |  |
| No. Days 7 |  |  |  |
| N | 2* | 0 | 0 |
| S | 0* | 0 | 0 |
| E | 13 | 0 | 0 |
| W | 3* | 0 | 0 |
| CP | 3* | 0 | 0 |
| Total | 21 | 0 | 0 |
| Average No. .4 |  |  |  |
| No. Days 7 |  |  |  |
| N | 0** | 0 | 0 |
| S | 0* | 0 | 0 |
| E | 0* | 0 | 0 |
| W | 2* | 0 | 0 |
| CP | 0* | 0 | 0 |
| Total | 2 | 0 | 0 |
| Average No. 1.8 |  |  |  |
| No. Days 7 |  |  |  |
| N | 0* | 0 | 0 |
| S | 6 | 0 | 0 |
| E | 0* | 0 | 0 |
| W | 0* | 0 | 0 |
| CP | 3* | 0 | 0 |
| Total | 9 | 0 | 0 |

*Top off
**Trap missing

| | Trap | Net | Ground |
|---|---|---|---|
| Average No. 63.6 |  |  |  |
| No. Days 7 |  |  |  |
| N | 111 | 0 | 0 |
| S | 17 | 0 | 0 |
| E | 86 | 0 | 0 |
| W | 47 | 0 | 0 |
| CP | 57 | 0 | 0 |
| Total | 318 | 0 | 0 |
| Average No. 60.1 |  |  |  |
| No. Days. 7 |  |  |  |
| N | 156 | 0 | 0 |
| S | 26 | 0 | 0 |
| E | 54 | 0 | 0 |
| W | 14 | 0 | 0 |
| CP | 56 | 0 | 0 |
| Total | 306 | 0 | 0 |
| Average No. 65.2 |  |  |  |
| No. Days 7 |  |  |  |
| N | 115 | 0 | 0 |
| S | 53 | 0 | 0 |
| E | 69 | 0 | 0 |
| W | 42 | 0 | 0 |
| CP | 47 | 1 | 0 |
| Total | 326 | 1 | 0 |
| Average No. 46.6 |  |  |  |
| No. Days 7 |  |  |  |
| N | 28 | 0 | 0 |
| S | 37 | 0 | 0 |
| E | 48 | 0 | 0 |
| W | 83 | 0 | 0 |
| CP | 37 | 0 | 0 |
| Total | 233 | 0 | 0 |
| Average No. 57 |  |  |  |
| No. Days 10 |  |  |  |
| N | 43 | 0 | 0 |
| S | 54 | 0 | 0 |
| E | 82 | 0 | 0 |
| W | 47 | 0 | 0 |
| CP | 59 | 0 | 0 |
| Total | 285 | 0 | 0 |
| Average No. 41.2 |  |  |  |
| No. Days 10 |  |  |  |
| N | 44 | 0 | 0 |
| S | 23 | 0 | 0 |
| E | 37 | 0 | 0 |
| W | 49 | 0 | 0 |
| CP | 52 | 0 | 0 |
| Total | 205 | 0 | 0 |
| Average No. 33 |  |  |  |
| No. Days 10 |  |  |  |
| N | 76 | 0 | 0 |
| S | 37 | 0 | 0 |
| E | 23 | 0 | 0 |

-continued

| | | Trap | Net | Ground |
|---|---|---|---|---|
| | W | 19 | 0 | 0 |
| | CP | 10 | 0 | 0 |
| Total | | 165 | 0 | 6 |
| Average No. | 67.3 | | | |
| No. Days | 10 | | | |
| | N | 57 | 0 | 0 |
| | S | 78 | 0 | 0 |
| | E | 54 | 0 | 0 |
| | W | 120 | 0 | 0 |
| | CP | 28 | 0 | 0 |
| Total | | 337 | 0 | 0 |
| Average No. | 18.4 | | | |
| No. Days | 6 | | | |
| | N | 16 | 0 | 0 |
| | S | 17 | 0 | 0 |
| | E | 27 | 0 | 0 |
| | W | 21 | 0 | 0 |
| | CP | 11 | 0 | 0 |
| Total | | 92 | 0 | 0 |
| Average No. | 5.8 | | | |
| No. Days | 6 | | | |
| | N | 10 | 0 | 0 |
| | S | 1 | 0 | 0 |
| | E | 7 | 0 | 0 |
| | W | 6 | 0 | 0 |
| | CP | 5 | 0 | 0 |
| Total | | 29 | 0 | 0 |
| Average No. | 15.4 | | | |
| No. Days | 6 | | | |
| | N | 34 | 0 | 0 |
| | S | 8 | 0 | 0 |
| | E | 16 | 0 | 0 |
| | W | 9 | 0 | 0 |
| | CP | 10 | 0 | 0 |
| Total | | 77 | 0 | 0 |
| Average No. | 38 | | | |
| No. Days | 6 | | | |
| | N | 36 | 0 | 0 |
| | S | 42 | 0 | 0 |
| | E | 36 | 0 | 0 |
| | W | 47 | 0 | 0 |
| | CP | 29 | 0 | 0 |
| Total | | 190 | 0 | 0 |
| Average No. | 18.8 | | | |
| No. Days | 6 | | | |
| | N | 9 | 0 | 0 |
| | S | 20 | 0 | 0 |
| | E | 33 | 0 | 0 |
| | W | 19 | 0 | 0 |
| | CP | 13 | 0 | 0 |
| Total | | 94 | 0 | 0 |
| Average No. | 7 | | | |
| No. Days | 6 | | | |
| | N | 8 | 0 | 0 |
| | S | 3 | 0 | 0 |
| | E | 8 | 0 | 0 |
| | W | 10 | 0 | 0 |
| | CP | 6 | 0 | 0 |
| Total | | 35 | 0 | 0 |
| Average No. | 9.6 | | | |
| No. Days | 6 | | | |
| | N | 26 | 0 | 0 |
| | S | 6 | 0 | 0 |
| | E | 3 | 0 | 0 |
| | W | 2 | 0 | 0 |
| | CP | 11 | 0 | 0 |
| Total | | 48 | 0 | 0 |
| Average No. | 25.4 | | | |
| No. Days | 6 | | | |
| | N | 36 | 0 | 0 |
| | S | 32 | 0 | 0 |
| | E | 13 | 0 | 0 |
| | W | 41 | 0 | 0 |
| | CP | 5 | 0 | 0 |
| Total | | 127 | 0 | 0 |
| Average No. | 10.6 | | | |
| No. Days | 7 | | | |
| | N | 10 | 0 | 0 |
| | S | 11 | 0 | 0 |
| | E | 15 | 1 | 0 |
| | W | 10 | 0 | 0 |
| | C | 7 | 0 | 0 |
| Total | | 53 | 1 | 0 |
| Average No. | 6 | | | |
| No. Days | 7 | | | |
| | N | 5 | 0 | 0 |
| | S | 5 | 0 | 0 |
| | E | 4 | 0 | 0 |
| | W | 3 | 0 | 0 |
| | C | 13 | 1 | 0 |
| Total | | 30 | 1 | 0 |
| Average No. | 14.8 | | | |
| No. Days | 7 | | | |
| | N | 36 | 0 | 0 |
| | S | 12 | 0 | 0 |
| | E | 10 | 0 | 0 |
| | W | 4 | 0 | 0 |
| | C | 12 | 0 | 0 |
| Total | | 74 | 0 | 0 |
| Average No. | 27.4 | | | |
| No. Days | 7 | | | |
| | N | 31 | 0 | 0 |
| | S | 27 | 0 | 0 |
| | E | 11 | 0 | 0 |
| | W | 47 | 0 | 0 |
| | E | 21 | 0 | 0 |
| Total | | 137 | 0 | 0 |
| Average No. | 31.6 | | | |
| No. Days | 7 | | | |
| | N | 24 | 0 | 0 |
| | S | 25 | 0 | 0 |
| | E | 48 | 0 | 0 |
| | W | 36 | 0 | 0 |
| | C | 25 | 0 | 0 |
| Total | | 158 | 0 | 0 |
| Average No. | 22.5 | | | |
| No. Days | 7 | | | |
| | N | 15 | 0 | 0 |
| | S | 18 | 0 | 0 |
| | E | 23 | 0 | 0 |
| | W | 22 | 0 | 0 |
| | C | 33 | 0 | 0 |
| Total | | 111 | 0 | 0 |
| Average No. | 13.6 | | | |
| No. Days | 7 | | | |
| | N | 23 | 0 | 0 |
| | S | 21 | 0 | 0 |
| | E | 13 | 0 | 0 |
| | W | 9 | 0 | 0 |
| | C | 2 | 0 | 0 |
| Total | | 68 | 0 | 0 |
| Average No. | 15 | | | |
| No. Days | 7 | | | |
| | N | 17 | 0 | 1 |
| | S | 14 | 0 | 0 |
| | E | 15 | 0 | 0 |

|   | Trap | Net | Ground |
|---|---|---|---|
| W | 16 | 0 | 0 |
| C | 13 | 0 | 0 |
| Total | 75 | 0 | 1 |
| Average No. | 21 | | |
| No. Days | 7 | | |
| N | 13 | 0 | 0 |
| S | 17 | 0 | 0 |
| E | 30 | 0 | 0 |
| W | 33 | 0 | 0 |
| C | 22 | 0 | 0 |
| Total | 105 | 0 | 0 |
| Average No. | 16.8 | | |
| No. Days | 7 | | |
| N | 17 | 0 | 0 |
| S | 10 | 0 | 0 |
| E | 10 | 0 | 0 |
| W | 21 | 0 | 0 |
| C | 26 | 0 | 0 |
| Total | 84 | 0 | 0 |
| Average No. | 16.8 | | |
| No. Days | 7 | | |
| N | 31 | 0 | 0 |
| S | 21 | 0 | 0 |
| E | 15 | 0 | 0 |
| W | 12 | 0 | 0 |
| C | 5 | 0 | 0 |
| Total | 84 | 0 | 0 |
| Average No. | 18 | | |
| No. Days | 7 | | |

4. Lure Comparison for Western and Northers Cornworm

This study compares nine different trap designs. Another study compares 12 different lure formulations. Lures were changed weekly and seasonally. The number of captures Western and Northern corn rootworm adults were calculated per trap per testing period.

Trap 1=clear top and bottom

Trap 2=clear top and white bottom

Trap 3=clear top and yellow bottom

Trap 4=Sutter trap

Trap 5=Concep trap

Trap 6=Pherocon AM with lure

Trap 7=Multigard with lure

Trap 8=Pherocon AM withot lure

Trap 9=Multigard without lute

Results:

There was no statistical difference between various designs, sutter and Concep (modified boll weevil trap) kairomone trap designs. Multigard sticky traps with kairomone lure were more attractive than other designs. But, non-sticky designs demonstrated excellent efficiency for seasonal monitoring of CRW.

Lures most attractive to Western and Northern CRW appeared to be attractive full season.

| | | Lure Comparison: Lures Changed Weekly - Western and Northern Corn Rootworm Adults Averaged Per Trap Per Sample Period. Field C1433A. 1997 | | | | | | |
|---|---|---|---|---|---|---|---|---|
| | | Day | | | | | | |
| Lure # | | 211 | 218 | 225 | 232 | 239 | 246 | 253 |
| 1 | WCR ♀ | 12.4 ± 6.1 | 1.7 ± 1.7 | 9.7 ± 8.7 | 14.0 ± 6.2 | 20.2 ± 18.2 | 28.3 ± 9.0 | 76.3 ± 16.0 |
| 8276 | WCR ♂ | 82.9 ± 35.7 | 11.3 ± 11.3 | 6.7 ± 5.7 | 5.7 ± 1.9 | 0.8 ± 0.8 | 0.3 ± 0.3 | 0 |
| | NCR ♀ | 14.1 ± 9.5 | 0.7 ± 0.7 | 3.3 ± 2.0 | 10.0 ± 6.2 | 7.3 ± 5.0 | 11.3 ± 7.7 | 69.3 ± 16.7 |
| | NCR ♂ | 74.2 ± 23.4 | 15.0 ± 12.5 | 8.7 ± 6.8 | 2.3 ± 0.9 | 0.3 ± 0.3 | 0.3 ± 0.3 | 0 |
| 3 | WCR ♀ | 0.7 ± 0.7 | 0.3 ± 0.3 | 1.0 ± 0.6 | 1.0 ± 0.6 | 13.0 ± 10.6 | 10.0 ± 4.2 | 14.3 ± 5.4 |
| 8326 | WCR ♂ | 13.7 ± 2.3 | 12.7 ± 4.8 | 22.0 ± 11.0 | 2.0 ± 1.5 | 0 | 0 | 0 |
| | NCR ♀ | 31.3 ± 22.3 | 0.3 ± 0.3 | 3.3 ± 0.3 | 9.7 ± 2.9 | 17.3 ± 15.3 | 80.3 ± 25.8 | 176.0 ± 44. |
| | NCR ♂ | 113.7 ± 53.8 | 7.0 ± 5.0 | 10.0 ± 0.6 | 4.0 ± 2.6 | 0 | 3.3 ± 3.3 | 1.3 ± 1.3 |
| 6 | WCR ♀ | 0.3 ± 0.3 | 0 | 1.3 ± 1.3 | 0.7 ± 0.3 | 7.0 ± 2.0 | 10.3 ± 3.9 | 16.7 ± 9.6 |
| 8280 | WCR ♂ | 7.0 ± 2.0 | 3.0 ± 1.7 | 5.7 ± 1.2 | 0.7 ± 0.3 | 0 | 0.3 ± 0.3 | 0.7 ± 0.3 |
| | NCR ♀ | 16.9 ± 14.2 | 0.3 ± 0.3 | 2.3 ± 0.3 | 6.0 ± 1.2 | 19.7 ± 6.1 | 24.7 ± 5.2 | 73.3 ± 24.2 |
| | NCR ♂ | 80.4 ± 31.9 | 0.7 ± 0.7 | 3.7 ± 1.2 | 4.0 ± 1.0 | 0 | 1.7 ± 1.2 | 0 |
| 7 | WCR ♀ | 0 | 1.3 ± 0.9 | 2.0 ± 1.0 | 2.7 ± 2.1 | 2.7 ± 1.5 | 1.0 ± 0.6 | 9.3 ± 2.3 |
| 8281 | WCR ♂ | 13.0 ± 12.5 | 22.3 ± 8.7 | 12.0 ± 9.2 | 7.0 ± 6.0 | 0 | 0 | 0 |
| | NCR ♀ | 1.8 ± 1.3 | 1.7 ± 1.2 | 1.3 ± 1.3 | 2.7 ± 1.3 | 4.3 ± 0.9 | 15.7 ± 8.7 | 85.7 ± 41.2 |
| | NCR ♂ | 17.9 ± 15.9 | 6.7 ± 3.7 | 4.7 ± 2.4 | 8.0 ± 5.0 | 0 | 1.3 ± 1.3 | 0 |
| 8 | WCR ♀ | 0 | 0 | 2.1 ± 1.7 | 0.3 ± 0.3 | 0.7 ± 0.3 | 1.0 ± 0.6 | 0.7 ± 0.7 |
| 8279 | WCR ♂ | 5.0 ± 3.0 | 4.7 ± 2.3 | 56.5 ± 8.9 | 3.3 ± 3.3 | 0 | 0.7 ± 0.7 | 0 |
| | NCR ♀ | 13.9 ± 5.2 | 2.5 ± 1.1 | 25.9 ± 3.4 | 28.0 ± 7.0 | 87.0 ± 18.1 | 193.1 ± 26.9 | 269.7 ± 48. |
| | NCR ♂ | 104.4 ± 28.2 | 35.8 ± 16.6 | 69.8 ± 18.0 | 16.3 ± 3.9 | 0 | 20.3 ± 7.9 | 0 |
| 11 | WCR ♀ | 1.0 ± 0.6 | 0 | 1.0 ± 0.6 | 0.3 ± 0.3 | 0 | 0 | 0 |
| 8390 | WCR ♂ | 6.3 ± 4.4 | 5.3 ± 1.9 | 18.7 ± 15.7 | 3.7 ± 2.7 | 0 | 0 | 0 |
| | NCR ♀ | 5.5 ± 4.0 | 0.7 ± 0.3 | 5.1 ± 3.2 | 19.9 ± 3.1 | 39.7 ± 15.3 | 115.2 ± 33.7 | 235.4 ± 7.2 |
| | NCR ♂ | 77.5 ± 33.4 | 17.7 ± 5.6 | 41.9 ± 16.3 | 20.1 ± 7.1 | 0.7 ± 0.7 | 6.2 ± 4.1 | 1.6 ± 1.6 |
| 12 | WCR ♀ | 12.6 ± 8.0 | 5.8 ± 1.4 | 29.4 ± 9.5 | 38.5 ± 10.3 | 90.9 ± 17.3 | 71.9 ± 20.0 | 84.7 ± 21.3 |
| 8391 | WCR ♂ | 205.7 ± 25.7 | 53.5 ± 10.4 | 85.3 ± 40.0 | 23.5 ± 3.8 | 0.4 ± 0.4 | 3.7 ± 2.0 | 0 |
| | NCR ♀ | 11.2 ± 6.5 | 0.3 ± 0.3 | 2.1 ± 1.2 | 8.0 ± 6.0 | 11.3 ± 2.3 | 25.0 ± 7.5 | 91.4 ± 32.6 |
| | NCR ♂ | 48.8 ± 12.6 | 13.0 ± 4.6 | 24.6 ± 14.6 | 3.7 ± 1.7 | 0.7 ± 0.7 | 0.7 ± 0.3 | 0.3 ± 0.3 |

Lure Comparison: Lures Changed Weekly - Western and Northern Corn Rootworm Adults Averaged Per Trap Per Sample Period. Field T411A. 1997

| Lure # | | Day | | | | | | |
|---|---|---|---|---|---|---|---|---|
| | | 212 | 219 | 226 | 233 | 240 | 247 | 254 |
| 1 | WCR ♀ | 0 | 0.3 ± 0.3 | 1.0 ± 0.6 | 2.7 ± 0.3 | 0.7 ± 0.3 | 4.3 ± 1.5 | 7.7 ± 3.0 |
| 8276 | WCR ♂ | 0.7 ± 0.3 | 1.0 ± 0.6 | 0.3 ± 0.3 | 1.0 ± 0.0 | 1.3 ± 1.3 | 1.3 ± 0.3 | 0 |
| | NCR ♀ | 0 | 0.7 ± 0.3 | 1.3 ± 1.3 | 3.0 ± 2.5 | 0 | 5.7 ± 2.6 | 8.7 ± 2.4 |
| | NCR ♂ | 0.3 ± 0.3 | 0.3 ± 0.3 | 1.7 ± 0.9 | 1.3 ± 0.7 | 0.3 ± 0.3 | 2.0 ± 0.6 | 1.3 ± 0.9 |
| 3 | WCR ♀ | 0 | 0 | 1.0 ± 1.0 | 1.3 ± 0.3 | 2.3 ± 1.2 | 2.3 ± 1.9 | 4.3 ± 1.3 |
| 8326 | WCR ♂ | 1.0 ± 1.0 | 1.0 ± 1.0 | 3.3 ± 1.7 | 1.0 ± 1.0 | 1.0 ± 0.6 | 2.0 ± 1.0 | 0 |
| | NCR ♀ | 0 | 1.3 ± 0.3 | 17.5 ± 13.6 | 16.0 ± 4.1 | 16.2 ± 3.9 | 26.7 ± 9.3 | 81.5 ± 21.9 |
| | NCR ♂ | 0.7 ± 0.3 | 2.3 ± 0.3 | 24.5 ± 14.8 | 21.0 ± 6.6 | 16.2 ± 8.2 | 16.7 ± 13.7 | 4.5 ± 0.3 |
| 6 | WCR ♀ | 0 | 0 | 0 | 0.7 ± 0.3 | 0 | 2.0 ± 2.0 | 3.0 ± 1.2 |
| 8280 | WCR ♂ | 0 | 0 | 0.3 ± 0.3 | 0 | 0 | 0.7 ± 0.3 | 0 |
| | NCR ♀ | 0 | 0 | 3.0 ± 1.5 | 2.7 ± 1.2 | 0.3 ± 0.3 | 2.3 ± 1.2 | 20.3 ± 3.4 |
| | NCR ♂ | 0.3 ± 0.3 | 0 | 0.7 ± 0.3 | 3.3 ± 0.3 | 1.7 ± 1.7 | 1.7 ± 0.3 | 1.0 ± 0.6 |
| 7 | WCR ♀ | 0 | 0 | 0 | 0 | 0 | 0 | 0.7 ± 0.7 |
| 8281 | WCR ♂ | 0 | 0 | 0 | 0.3 ± 0.3 | 0 | 0 | 0 |
| | NCR ♀ | 0 | 0 | 0 | 1.0 ± 0.6 | 2.0 ± 1.5 | 4.7 ± 0.3 | 31.7 ± 11.4 |
| | NCR ♂ | 1.0 ± 0.6 | 0 | 0.3 ± 0.3 | 2.7 ± 1.2 | 1.7 ± 0.3 | 2.0 ± 1.5 | 1.0 ± 0.6 |
| 8 | WCR ♀ | 0 | 0 | 0 | 0.3 ± 0.3 | 0 | 1.3 ± 1.3 | 0 |
| 8279 | WCR ♂ | 0 | 5.0 ± 5.0 | 5.7 ± 5.2 | 7.0 ± 6.0 | 2.3 ± 1.2 | 0 | 1.0 ± 1.0 |
| | NCR ♀ | 0.3 ± 0.3 | 6.3 ± 1.9 | 15.8 ± 4.1 | 24.1 ± 6.3 | 22.2 ± 6.3 | 68.1 ± 23.6 | 168.8 ± 29. |
| | NCR ♂ | 5.7 ± 2.0 | 22.0 ± 9.0 | 50.2 ± 22.6 | 39.6 ± 21.6 | 44.1 ± 2.9 | 28.9 ± 12.6 | 22.0 ± 9.9 |

Lure Comparison: Lures Out All Summer - Western and Northern Corn Rootworm Adults Averaged Per Trap Per Sample Period. Field T411A. 1997

| Lure # | | Day | | | | | | |
|---|---|---|---|---|---|---|---|---|
| | | 212 | 219 | 226 | 233 | 240 | 247 | 254 |
| 1 | WCR ♀ | 0 | 0 | 5.5 ± 4.8 | 1.0 ± 0.4 | 1.8 ± 0.9 | 4.8 ± 2.8 | 9.8 ± 2.5 |
| 8276 | WCR ♂ | 0.3 ± 0.3 | 0 | 1.3 ± 0.9 | 2.0 ± 1.4 | 0.3 ± 0.3 | 1.3 ± 0.9 | 0.3 ± 0.3 |
| | NCR ♀ | 0 | 0.3 ± 0.3 | 6.8 ± 5.8 | 3.0 ± 1.4 | 1.3 ± 0.9 | 6.3 ± 3.7 | 11.0 ± 3.2 |
| | NCR ♂ | 3.0 ± 1.8 | 1.5 ± 0.6 | 2.0 ± 0.9 | 7.8 ± 3.9 | 1.8 ± 1.0 | 6.0 ± 4.7 | 0.8 ± 0.5 |
| 2 | WCR ♀ | 0 | 0 | 0 | 0 | 0 | 0.5 ± 0.5 | 1.8 ± 0.5 |
| 8291T | WCR ♂ | 0.5 ± 0.3 | 0.8 ± 0.5 | 1.8 ± 1.8 | 0.5 ± 0.3 | 0.5 ± 0.5 | 0.3 ± 0.3 | 0.3 ± 0.3 |
| | NCR ♀ | 0.5 ± 0.3 | 1.0 ± 0.6 | 3.3 ± 1.5 | 5.5 ± 1.8 | 5.5 ± 1.8 | 4.3 ± 2.4 | 82.9 ± 17.9 |
| | NCR ♂ | 2.0 ± 0.8 | 3.3 ± 1.8 | 11.8 ± 8.8 | 8.8 ± 4.6 | 8.8 ± 4.6 | 5.0 ± 3.7 | 14.4 ± 8.2 |
| 3 | WCR ♀ | 0 | 0 | 2.3 ± 1.9 | 1.3 ± 0.9 | 0 | 1.8 ± 0.8 | 1.8 ± 0.6 |
| 8326 | WCR ♂ | 0.3 ± 0.3 | 1.3 ± 0.8 | 1.0 ± 0.7 | 7.3 ± 4.5 | 0.5 ± 0.5 | 0.5 ± 0.5 | 0 |
| | NCR ♀ | 0 | 2.8 ± v1.5 | 15.2 ± 12.2 | 18.2 ± 8.7 | 8.0 ± 2.4 | 42.0 ± 15.5 | 103.0 ± 37.7 |
| | NCR ♂ | 1.0 ± 0.7 | 6.8 ± 4.3 | 2.6 ± 1.9 | 21.1 ± 10.1 | 7.0 ± 2.4 | 3.0 ± 0.8 | 3.0 ± 4.4 |
| 4 | WCR ♀ | 0 | 0 | 0.3 ± 0.3 | 0.3 ± 0.3 | 0.3 ± 0.3 | 0.8 ± 0.5 | 5.5 ± 3.3 |
| 8336 | WCR ♂ | 0 | 0 | 0.5 ± 0.5 | 0 | 0 | 0.3 ± 0.3 | 0 |
| | NCR ♀ | 0 | 0.3 ± 0.3 | 8.5 ± 7.8 | 5.2 ± 2.5 | 2.0 ± 1.1 | 13.5 ± 7.1 | 41.6 ± 14.4 |
| | NCR ♂ | 0.8 ± 0.5 | 0.3 ± 0.3 | 4.8 ± 3.8 | 4.8 ± 3.1 | 2.0 ± 1.4 | 1.3 ± 0.5 | 5.6 ± 2.6 |
| 5 | WCR ♀ | 0 | 0.8 ± 0.3 | 1.3 ± 0.5 | 3.0 ± 1.1 | 0.8 ± 0.5 | 6.5 ± 2.3 | 24.3 ± 3.6 |
| 8337 | WCR ♂ | 1.5 ± 0.5 | 4.0 ± 2.4 | 3.3 ± 1.7 | 6.5 ± 3.0 | 16.5 ± 7.0 | 1.8 ± 1.4 | 1.8 ± 0.5 |
| | NCR ♀ | 0 | 4.0 ± 1.3 | 6.0 ± 3.7 | 12.3 ± 6.6 | 16.3 ± 6.0 | 49.7 ± 15.0 | 105.3 ± 19.0 |
| | NCR ♂ | 2.3 ± 0.9 | 14.0 ± 7.2 | 11.8 ± 4.7 | 23.4 ± 13.1 | 15.0 ± 9.4 | 7.1 ± 3.5 | 7.2 ± 4.1 |
| 11 | WCR ♀ | 0 | 0 | 1.0 ± 1.0 | 1.0 ± 0.6 | 3.3 ± 3.3 | 0 | 13.0 ± 13.0 |
| 8390 | WCR ♂ | 0 | 0.3 ± 0.3 | 3.0 ± 1.5 | 17.0 ± 2.0 | 3.7 ± 1.5 | 1.0 ± 1.0 | 0.3 ± 0.3 |
| | NCR ♀ | 0 | 1.7 ± 0.3 | 25.8 ± 19.5 | 32.8 ± 4.9 | 25.7 ± 2.3 | 63.8 ± 15.5 | 83.0 ± 58.0 |
| | NCR ♂ | 1.7 ± 1.2 | 3.7 ± 1.5 | 30.2 ± 6.8 | 39.9 ± 7.0 | 59.7 ± 20.1 | 38.2 ± 19.8 | 11.0 ± 10.5 |
| 12 | WCR ♀ | 0 | 1.7 ± 0.3 | 2.7 ± 0.7 | 6.3 ± 1.3 | 1.7 ± 1.7 | 10.7 ± 3.5 | 19.3 ± 4.6 |
| 8276 | WCR ♂ | 0.7 ± 0.7 | 2.0 ± 1.2 | 2.3 ± 1.2 | 11.0 ± 1.5 | 12.3 ± 3.5 | 3.7 ± 1.3 | 1.7 ± 1.7 |
| | NCR ♀ | 0.3 ± 0.3 | 0.7 ± 0.7 | 3.7 ± 0.9 | 14.7 ± 2.4 | 4.3 ± 3.0 | 12.3 ± 2.0 | 32.3 ± 6.5 |
| | NCR ♂ | 0 | 1.3 ± 0.7 | 9.3 ± 6.4 | 37.3 ± 14.3 | 13.3 ± 7.9 | 6.7 ± 3.7 | 2.0 ± 0.6 |
| 6 | WCR ♀ | 0 | 0 | 1.5 ± 1.5 | 0.3 ± 0.3 | 0.8 ± 0.5 | 0.5 ± 0.5 | 2.5 ± 1.0 |
| 8280 | WCR ♂ | 0 | 0 | 4.0 ± 3.7 | 1.0 ± 1.0 | 0.3 ± 0.3 | 0 | 0.3 ± 0.3 |
| | NCR ♀ | 0.3 ± 0.3 | 0 | 6.2 ± 3.5 | 1.8 ± 1.2 | 2.3 ± 0.9 | 3.0 ± 1.2 | 21.8 ± 7.1 |
| | NCR ♂ | 2.3 ± 1.4 | 1.0 ± 0.4 | 21.3 ± 19.6 | 5.3 ± 3.5 | 1.0 ± 0.4 | 1.0 ± 0.7 | 2.5 ± 1.6 |
| 7 | WCR ♀ | 0 | 0 | 0 | 0 | 0 | 0 | 0.8 ± 0.5 |
| 8281 | WCR ♂ | 0 | 0.3 ± 0.3 | 0.3 ± 0.3 | 0 | 0 | 0 | 0.3 ± 0.3 |
| | NCR ♀ | 0 | 0 | 1.3 ± 0.8 | 0.3 ± 0.3 | 1.0 ± 0.7 | 4.0 ± 0.7 | 16.0 ± 3.5 |
| | NCR ♂ | 0.5 ± 0.3 | 0.8 ± 0.5 | 4.0 ± 3.4 | 0.5 ± 0.3 | 1.0 ± 0.4 | 2.3 ± 0.6 | 4.0 ± 3.3 |
| 8 | WCR ♀ | 0 | 0 | 5.3 ± 5.3 | 1.8 ± 0.5 | 0 | 0.8 ± 0.8 | 0.3 ± 0.3 |
| 8279 | WCR ♂ | 0 | 5.0 ± 3.1 | 9.8 ± 4.1 | 24.5 ± 4.6 | 7.0 ± 4.5 | 0 | 0 |
| | NCR ♀ | 0.3 ± 0.3 | 6.6 ± 2.3 | 27.8 ± 9.7 | 46.4 ± 12.3 | 60.8 ± 15.5 | 190.0 ± 32.5 | 296.4 ± 38. |
| | NCR ♂ | 4.5 ± 2.4 | 31.9 ± 12.7 | 55.5 ± 30.4 | 61.9 ± 7.9 | 59.2 ± 23.2 | 33.5 ± 16.4 | 25.6 ± 6.6 |

Lure Comparison: Lures Out All Summer - Western and Northern Corn
Rootworm Adults Averaged Per Trap Per Sample Period. Field T411A.
1997

| Lure # | | Day 212 | 219 | 226 | 233 | 240 | 247 | 254 |
|---|---|---|---|---|---|---|---|---|
| 9 | WCR ♀ | 0 | 0 | 0 | 0.3 ± 0.3 | 0 | 1.3 ± 0.8 | 1.3 ± 0.5 |
| 8347 | WCR ♂ | 0 | 0 | 2.5 ± 1.9 | 7.0 ± 2.9 | 0.3 ± 0.3 | 0.3 ± 0.3 | 0 |
| | NCR ♀ | 0.3 ± 0.3 | 0.8 ± 0.3 | 3.1 ± 0.9 | 15.0 ± 4.8 | 16.5 ± 3.5 | 59.2 ± 13.7 | 97.9 ± 17.2 |
| | NCR ♂ | 1.0 ± 0.4 | 5.5 ± 3.9 | 22.7 ± 13.2 | 34.5 ± 11.6 | 12.0 ± 1.5 | 6.6 ± 2.8 | 13.1 ± 4.1 |
| 10 | WCR ♀ | 0 | 0 | 1.8 ± 0.9 | 5.8 ± 2.3 | 0.8 ± 0.5 | 4.8 ± 1.4 | 30.0 ± 12.2 |
| 8282 | WCR ♂ | 1.3 ± 0.8 | 0.8 ± 0.3 | 3.0 ± 2.7 | 12.0 ± 5.2 | 7.5 ± 2.9 | 0.8 ± 0.3 | 1.8 ± 0.9 |
| | NCR ♀ | 0 | 0.3 ± 0.3 | 1.0 ± 0.4 | 6.6 ± 3.3 | 2.0 ± 0.4 | 2.0 ± 0.7 | 15.0 ± 1.8 |
| | NCR ♂ | 1.3 ± 1.3 | 1.3 ± 0.9 | 10.8 ± 9.4 | 23.9 ± 12.0 | 2.8 ± 1.5 | 2.0 ± 0.9 | 0.8 ± 0.5 |
| 11 | WCR ♀ | 0 | 0 | 1.8 ± 1.4 | 0.3 ± 0.3 | 0 | 0.3 ± 0.3 | 0.5 ± 0.5 |
| 8390 | WCR ♂ | 0.3 ± 0.3 | 5.5 ± 3.2 | 4.5 ± 3.2 | 8.8 ± 4.7 | 3.8 ± 3.8 | 0.5 ± 0.5 | 0 |
| | NCR ♀ | 0 | 4.8 ± 1.9 | 15.9 ± 12.5 | 15.6 ± 5.8 | 24.9 ± 4.6 | 63.7 ± 8.8 | 132.8 ± 16.7 |
| | NCR ♂ | 1.5 ± 0.3 | 7.5 ± 2.2 | 21.4 ± 12.3 | 27.2 ± 6.5 | 28.1 ± 7.6 | 14.5 ± 7.3 | 16.0 ± 7.0 |
| 12 | WCR ♀ | 0 | 0.5 ± 0.5 | 3.8 ± 2.3 | 6.3 ± 1.9 | 9.0 ± 5.5 | 18.5 ± 3.1 | 43.6 ± 11.4 |
| 8391 | WCR ♂ | 3.8 ± 1.0 | 4.8 ± 4.1 | 5.5 ± 1.8 | 9.0 ± 3.2 | 10.0 ± 3.1 | 3.3 ± 2.0 | 2.1 ± 0.7 |
| | NCR ♀ | 0 | 1.3 ± 1.3 | 4.0 ± 1.6 | 5.0 ± 0.7 | 4.0 ± 0.0 | 20.3 ± 4.9 | 29.5 ± 4.9 |
| | NCR ♂ | 1.0 ± 0.4 | 2.0 ± 1.7 | 10.3 ± 8.3 | 7.5 ± 2.7 | 10.0 ± 5.3 | 3.5 ± 2.9 | 1.8 ± 1.1 |

Lure Comparison: Lures Out All Summer - Western and Northern Corn
Rootworm Adults Averaged Per Trap Per Sample Period. Field C1433A.
1997

| Lure # | | Day 211 | 218 | 225 | 232 | 239 | 246 | 253 |
|---|---|---|---|---|---|---|---|---|
| 1 | WCR ♀ | 4.5 ± 1.6 | 2.9 ± 0.9 | 5.5 ± 2.8 | 7.5 ± 3.1 | 15.3 ± 5.8 | 9.5 ± 2.9 | 37.8 ± 6.2 |
| 8276 | WCR ♂ | 65.5 ± 17.1 | 21.6 ± 17.3 | 12.5 ± 4.3 | 11.5 ± 5.4 | 0 | 0.3 ± 0.3 | 0.8 ± 0.5 |
| | NCR ♀ | 6.2 ± 1.3 | 0.5 ± 0.3 | 0.5 ± 0.5 | 2.8 ± 1.0 | 3.5 ± 1.2 | 6.3 ± 2.5 | 14.8 ± 1.9 |
| | NCR ♂ | 56.8 ± 20.3 | 9.5 ± 7.5 | 8.8 ± 3.3 | 5.5 ± 3.9 | 0.3 ± 0.3 | 1.5 ± 0.9 | 1.0 ± 0.4 |
| 2 | WCR ♀ | 1.0 ± 0.7 | 0.5 ± 0.5 | 1.8 ± 0.9 | 0.8 ± 0.5 | 1.3 ± 0.5 | 4.0 ± 1.0 | 2.5 ± 1.2 |
| 8291T | WCR ♂ | 30.0 ± 4.3 | 8.8 ± 3.8 | 8.8 ± 3.8 | 2.5 ± 2.2 | 0 | 0.5 ± 0.5 | 0.3 ± 0.3 |
| | NCR ♀ | 18.8 ± 6.4 | 0.5 ± 0.3 | 4.8 ± 2.6 | 8.0 ± 2.4 | 29.8 ± 6.6 | 37.1 ± 4.1 | 100.0 ± 13.6 |
| | NCR ♂ | 72.2 ± 11.2 | 5.0 ± 2.5 | 14.5 ± 5.7 | 3.8 ± 0.6 | 0.3 ± 0.3 | 6.2 ± 3.2 | 0.8 ± 0.5 |
| 3 | WCR ♀ | 2.0 ± 1.7 | 0.5 ± 0.5 | 0.5 ± 0.3 | 0.8 ± 0.8 | 4.8 ± 1.9 | 6.8 ± 2.0 | 9.0 ± 2.6 |
| 8326 | WCR ♂ | 19.0 ± 5.8 | 10.0 ± 1.7 | 17.5 ± 6.1 | 0.3 ± 0.3 | 0 | 0.3 ± 0.3 | 0 |
| | NCR ♀ | 20.1 ± 3.3 | 0.3 ± 0.3 | 1.8 ± 0.9 | 7.5 ± 1.4 | 33.3 ± 2.9 | 45.8 ± 18.4 | 87.8 ± 23.6 |
| | NCR ♂ | 80.1 ± 14.0 | 4.3 ± 1.3 | 12.3 ± 6.8 | 4.0 ± 2.2 | 0 | 0.3 ± 0.3 | 1.0 ± 0.7 |
| 4 | WCR ♀ | 1.8 ± 0.9 | 0.3 ± 0.3 | 4.7 ± 2.9 | 1.3 ± 0.8 | 3.3 ± 2.0 | 4.3 ± 2.6 | 18.5 ± 12.9 |
| 8336 | WCR ♂ | 15.8 ± 8.5 | 3.8 ± 1.7 | 16.9 ± 10.6 | 1.3 ± 1.3 | 0 | 0.3 ± 0.3 | 0.3 ± 0.3 |
| | NCR ♀ | 11.6 ± 7.3 | 0 | 2.3 ± 1.1 | 1.3 ± 0.6 | 9.5 ± 2.1 | 17.5 ± 6.8 | 56.2 ± 13.7 |
| | NCR ♂ | 55.1 ± 33.3 | 3.8 ± 2.1 | 9.3 ± 4.1 | 1.0 ± 0.0 | 0 | 0.8 ± 0.5 | 0.9 ± 0.9 |
| 5 | WCR ♀ | 6.8 ± 2.9 | 2.7 ± 0.9 | 9.8 ± 3.5 | 8.8 ± 4.2 | 53.5 ± 7.7 | 34.7 ± 5.5 | 36.5 ± 13.9 |
| 8337 | WCR ♂ | 86.7 ± 31.6 | 34.8 ± 11.7 | 67.2 ± 27.4 | 10.5 ± 4.9 | 0 | 0.5 ± 0.3 | 0 |
| | NCR ♀ | 7.5 ± 3.5 | 1.0 ± 0.6 | 4.5 ± 2.4 | 3.3 ± 2.1 | 12.8 ± 1.4 | 20.8 ± 4.9 | 46.5 ± 17.3 |
| 6 | WCR ♀ | 0.5 ± 0.5 | 0.3 ± 0.3 | 1.5 ± 0.9 | 0.3 ± 0.3 | 1.3 ± 0.3 | 2.3 ± 0.5 | 2.5 ± 1.3 |
| 8280 | WCR ♂ | 15.0 ± 7.5 | 10.3 ± 5.8 | 6.3 ± 3.4 | 0.3 ± 0.3 | 0 | 0 | 0 |
| | NCR ♀ | 12.3 ± 8.2 | 0.3 ± 0.3 | 0.8 ± 0.5 | 0.5 ± 0.5 | 3.3 ± 0.5 | 3.8 ± 1.9 | 15.3 ± 4.0 |
| | NCR ♂ | 64.0 ± 24.1 | 4.5 ± 2.3 | 3.5 ± 1.4 | 0.8 ± 0.3 | 0 | 0.8 ± 0.5 | 0 |
| 7 | WCR ♀ | 2.6 ± 1.2 | 0.3 ± 0.3 | 1.5 ± 0.3 | 0.3 ± 0.3 | 0.3 ± 0.3 | 1.0 ± 0.7 | 2.8 ± 1.5 |
| 8281 | WCR ♂ | 20.7 ± 10.2 | 19.3 ± 6.8 | 12.3 ± 7.9 | 1.0 ± 0.7 | 0 | 0 | 0 |
| | NCR ♀ | 3.2 ± 0.7 | 2.0 ± 0.7 | 0.5 ± 0.5 | 0.3 ± 0.3 | 3.5 ± 0.6 | 9.3 ± 3.7 | 83.5 ± 37.9 |
| | NCR ♂ | 32.1 ± 11.3 | 8.3 ± 5.4 | 8.8 ± 7.2 | 1.3 ± 0.6 | 0.3 ± 0.3 | 1.3 ± 0.9 | 2.3 ± 1.3 |
| 8 | WCR ♀ | 2.0 ± 1.1 | 1.0 ± 0.4 | 3.5 ± 2.0 | 0 | 0 | 0 | 0.3 ± 0.3 |
| 8279 | WCR ♂ | 22.5 ± 9.9 | 17.8 ± 7.3 | 28.5 ± 10.1 | 2.5 ± 1.3 | 0 | 0 | 0 |
| | NCR ♀ | 6.6 ± 1.8 | 2.8 ± 1.9 | 10.6 ± 3.8 | 35.5 ± 11.5 | 79.8 ± 36.6 | 127.5 ± 38.2 | 153.0 ± 41.9 |
| | NCR ♂ | 66.4 ± 13.0 | 24.2 ± 9.4 | 43.7 ± 13.5 | 19.7 ± 8.0 | 0 | 14.3 ± 6.5 | 2.2 ± 1.3 |
| 9 | WCR ♀ | 0.3 ± 0.3 | 0 | 1.0 ± 0.7 | 0.5 ± 0.3 | 1.0 ± 0.6 | 14.5 ± 9.6 | 2.0 ± 1.2 |
| 8347 | WCR ♂ | 12.3 ± 2.7 | 4.0 ± 1.5 | 8.3 ± 5.4 | 0.8 ± 0.5 | 0 | 0.3 ± 0.3 | 0 |
| | NCR ♀ | 18.3 ± 5.2 | 0.8 ± 0.5 | 2.8 ± 1.3 | 13.3 ± 4.5 | 31.5 ± 6.9 | 53.5 ± 17.4 | 144.6 ± 23.7 |
| | NCR ♂ | 64.2 ± 13.0 | 3.0 ± 1.7 | 13.8 ± 8.8 | 6.8 ± 2.6 | 0.5 ± 0.5 | 7.0 ± 3.7 | 6.4 ± 4.1 |
| 10 | WCR ♀ | 37.0 ± 24.3 | 1.5 ± 0.6 | 18.0 ± 12.5 | 26.6 ± 10.0 | 50.3 ± 12.9 | 61.6 ± 35.0 | 55.6 ± 3.3 |
| 8282 | WCR ♂ | 155.5 ± 50.5 | 24.8 ± 1.7 | 45.2 ± 9.4 | 11.6 ± 3.2 | 0 | 3.6 ± 0.6 | 1.6 ± 1.0 |
| | NCR ♀ | 6.4 ± 5.1 | 0.8 ± 0.5 | 2.5 ± 1.3 | 1.5 ± 0.9 | 1.5 ± 0.6 | 13.8 ± 9.1 | 18.0 ± 0.8 |
| | NCR ♂ | 27.4 ± 11.5 | 2.5 ± 1.3 | 18.0 ± 5.6 | 4.8 ± 2.1 | 0 | 1.3 ± 0.9 | 1.0 ± 0.6 |
| 11 | WCR ♀ | 0.5 ± 0.5 | 1.0 ± 1.0 | 2.0 ± 1.7 | 0.3 ± 0.3 | 1.3 ± 0.5 | 2.0 ± 0.9 | 3.5 ± 1.2 |
| 8390 | WCR ♂ | 15.7 ± 11.5 | 6.5 ± 2.7 | 31.5 ± 26.2 | 1.3 ± 0.8 | 0 | 0 | 0.5 ± 0.5 |
| | NCR ♀ | 12.7 ± 5.1 | 0.5 ± 0.5 | 3.3 ± 2.6 | 7.8 ± 2.7 | 38.3 ± 14.9 | 87.1 ± 16.0 | 171.6 ± 13. |
| | NCR ♂ | 50.1 ± 18.1 | 5.0 ± 1.8 | 13.3 ± 8.4 | 5.0 ± 1.7 | 0 | 3.2 ± 1.3 | 1.7 ± 1.0 |

-continued

Lure Comparison: Lures Out All Summer - Western and Northern Corn Rootworm Adults Averaged Per Trap Per Sample Period. Field C1433A. 1997

| Lure # | | Day | | | | | | |
|---|---|---|---|---|---|---|---|---|
| | | 211 | 218 | 225 | 232 | 239 | 246 | 253 |
| 12 | WCR ♀ | 23.8 ± 10.1 | 9.4 ± 2.9 | 17.5 ± 5.7 | 29.0 ± 4.0 | 93.0 ± 12.9 | 93.0 ± 15.2 | 106.7 ± 2 |
| 8391 | WCR ♂ | 153.7 ± 38.6 | 71.6 ± 18.6 | 52.6 ± 11.9 | 12.3 ± 3.6 | 0 | 3.5 ± 0.5 | 1.5 ± 0.9 |
| | NCR ♀ | 6.9 ± 4.4 | 1.3 ± 0.3 | 1.8 ± 0.3 | 5.5 ± 1.8 | 8.0 ± 1.1 | 21.3 ± 4.0 | 52.5 ± 5 |
| | NCR ♂ | 21.8 ± 8.4 | 4.0 ± 1.8 | 11.0 ± 2.4 | 2.5 ± 0.9 | 0.3 ± 0.3 | 3.3 ± 1.3 | 0.3 ± 0 |

What is claimed:

1. An insect trap suitable for capture of corn rootworm flying insect pest comprising:
   (a) a capture top dome containing a bait in a bait holder positioned in the center of the top dome;
   (b) a capture reservoir comprising
      (i) one or more locking devices enabling attachment of the capture reservoir to the capture top dome;
      (ii) a circular groove positioned in the center of the bottom of the capture reservoir allowing emplacement of the trap on a field stake;
   (c) a kairomone lure dispenser attached to the capture top dome.

2. The trap of claim 1 additionally comprising hanging attachment.

3. The trap of claim 2 wherein the top dome and the capture reservoir are made of polyethylene or polyvinylchloride.

4. The trap of claim 3 wherein the hanging attachment is a hanger tap integrally connected with the bait holder.

5. The trap of claim 4 wherein the hanger tap has an insert opening for attachment of a hanger.

6. The trap of claim 5 wherein the hanger is a plastic coated wire hanger.

7. The trap of claim 6 wherein the locking device is a locking tab.

8. The trap of claim 7 wherein the kairomone lure dispenser comprises a seal consisting of an inner layer of plastic and an outer layer of foil.

9. The trap of claim 8 wherein the kairomone lure dispenser is connected with the top dome through a side slot.

10. The trap of claim 9 wherein the lure is a kairomone-based attractant.

11. The trap of claim 10 wherein the kairomone lure is selected from the group consisting of 1, 2, 4-trimethoxybenzene, indole, transcimamaldehyde, eugenol, 4-methoxyphenethanol and 4-methoxycinnamaldehyde or a mixture thereof.

12. The trap of claim 11 wherein the bait is a kill bait.

13. The trap of claim 12 wherein the kill bait consists of a pill containing a feeding stimulating compound and an insecticide.

14. The trap of claim 13 wherein the feeding stimulating compound is cucurbitacin and insecticide is carbaryl.

* * * * *